United States Patent
Gupta et al.

(10) Patent No.: US 10,758,184 B2
(45) Date of Patent: Sep. 1, 2020

(54) SELF-OPERABLE, NON-INVASIVE, NON-CONTACT BIO-SIGNAL MONITORING

(71) Applicants: WASHINGTON STATE UNIVERSITY, Pullman, WA (US); Kavita Shashank Gupta, Pullman, WA (US)

(72) Inventors: Subhanshu Gupta, Pullman, WA (US); Kavita Shashank Gupta, Raipur (IN)

(73) Assignees: WASHINGTON STATE UNIVERSITY, Pullman, WA (US); PT. JNM MEDICAL COLLEGE, Chhattisgarh, IN (US)

( * ) Notice: Subject to any disclaimer, the term of this patent is extended or adjusted under 35 U.S.C. 154(b) by 289 days.

(21) Appl. No.: 15/197,874

(22) Filed: Jun. 30, 2016

(65) Prior Publication Data
US 2018/0000415 A1    Jan. 4, 2018

(51) Int. Cl.
*A61N 1/365*    (2006.01)
*A61N 1/37*    (2006.01)
*A61B 5/00*    (2006.01)
*A61B 5/0428*    (2006.01)
*A61B 5/0478*    (2006.01)
*A61B 5/0492*    (2006.01)
(Continued)

(52) U.S. Cl.
CPC ............ *A61B 5/684* (2013.01); *A61B 5/0478* (2013.01); *A61B 5/04085* (2013.01); *A61B 5/0492* (2013.01); *A61B 5/0496* (2013.01); *A61B 5/04286* (2013.01); *A61B 5/6804* (2013.01); *A61B 5/6823* (2013.01); *A61B 5/6831* (2013.01); *A61B 5/743* (2013.01); *A61B 5/0533* (2013.01)

(58) Field of Classification Search
CPC .......... A63F 13/06; A63F 13/10; A63F 13/42; A63F 13/213; A63F 13/40; A63F 13/212; A63F 13/428; A63F 2300/1012; A63F 2300/1093; A63F 2300/609
USPC .......................................................... 463/36
See application file for complete search history.

(56) References Cited

U.S. PATENT DOCUMENTS 3,954,100 A    5/1976   Sem-Jacobsen
4,606,352 A    8/1986   Geddes et al.
(Continued)

OTHER PUBLICATIONS

Yoo, Jerald, Long Yan, Seulki Lee, Hyejung Kim, and Hoi-Jun Yoo. "A wearable ECG acquisition system with compact planar-fashionable circuit board-based shirt" Information Technology in Biomedicine, IEEE Transactions on 13, No. 6 (2009): 897-902.

Primary Examiner — Jon Eric C Morales
(74) Attorney, Agent, or Firm — W&C IP

(57) ABSTRACT

Unique methods and bio-imaging systems are introduced herein for self-automated self-operable biomedical devices and methods for bio-signal monitoring, such as electrocardiograms (ECG), heart rate, and other vital signs, requiring no trained medical assistance or minimal assistance. In particular, methods and devices disclosed herein may require no dedicated medical resources, generate diagnostic quality results, and provide for motion artifact correction without inducing discomfort or irritation. Moreover, long term recording is realizable. Such methods and devices reduce the backlog of patients at out-patient wards as well as emergency response in remote areas.

16 Claims, 18 Drawing Sheets

(51) Int. Cl.
    *A61B 5/0496*     (2006.01)
    *A61B 5/0408*     (2006.01)
    *A61B 5/053*     (2006.01)

(56) References Cited

U.S. PATENT DOCUMENTS

| | | |
|---|---|---|
| 8,509,882 B2 | 8/2013 | Albert et al. |
| 8,688,189 B2 | 4/2014 | Shennib |
| 9,149,228 B2 | 10/2015 | Kinast |
| 9,597,567 B1 * | 3/2017 | Tran ................... A63B 60/46 |
| 2004/0087366 A1 * | 5/2004 | Shum ................... A63F 13/06 |
| | | 463/36 |
| 2015/0065842 A1 * | 3/2015 | Lee ................... A61B 5/04085 |
| | | 600/388 |
| 2017/0246460 A1 * | 8/2017 | Ghosh ................ A61N 1/36585 |

* cited by examiner

SELF-OPERABLE, NON-INVASIVE, NON-CONTACT BIO-SIGNAL MONITORING

FIELD OF THE INVENTION

The invention relates to self-operable (or self-assisted) bio-signal (e.g., vital signs) monitoring of multi-channel, multi-modal bio-signals including electroencephalography (EEG), electrocardiography (ECG), electromyography (EMG), and electrooculography (EOG). In particular, some exemplary embodiments relate to accurate and reproducible placement of sensors for recording multi-channel bio-signals.

BACKGROUND

The global Diagnostic ECG Market is estimated to reach $5,435 million by 2020 at a high compound annual growth rate (CAGR) during the forecast period. The factors driving this market include the increasing geriatric population, rising incidences of lifestyle diseases, technological advancements in diagnostic ECG devices, and high growth rate in developing countries. The factors restraining this market include the unstable reimbursement regulations, economic instability, and market saturation in the developed countries. Projections from Center for Disease Control and Prevention highlight that about 600,000 people die of heart disease in the United States every year—that's 1 in every 4 deaths. Coronary heart disease alone costs the United States $108.9 billion each year. This total includes the cost of health care services, medications, and lost productivity. More than 50% of people dying from heart disease pass away in an emergency department or prior to reaching a hospital.

To address such issues, the coordination of personnel, equipment, expert opinion, pre-hospital treatment, and capacity of health centers involved in responding in a timely manner presents a number of difficulties not only during emergencies but also towards daily healthcare. The long turnaround times for a routine check-up encourages people to postpone their cardiac check-up until later, aggravating the symptoms further. Emergency medical services (EMS) systems lacking sufficient resources even for day-to-day operations are overwhelmed in the event of a large-scale disaster. It's even harder on children as they react differently to emergencies than do adults because of anatomical, physiological, developmental, and emotional differences. Heart-rate and electrocardiograms (ECG) are the two most standard references to diagnose a patient during an emergency, pre-hospitalization, or post-hospitalization. Conventional ECG techniques require the physical presence of the patient in a hospital where the patient is assisted by an expert medical professional such as a nurse or para-medical staff. The necessity of using a dedicated medical facility and professional assistance consumes space, time, and resources (e.g., personnel resources) of the medical care provider. In addition, prolonged usage of conventional ECG methods and systems can cause skin irritation, discomfort, and rashes.

Though other existing bio-medical imaging methods, such as electromagnetic-based monitoring systems, laser-based monitoring systems, and image-based monitoring systems, have been demonstrated with good results and accuracy, they are sensitive to perspiration, muscle twitching, and distance from the receiver. Further, such systems are expensive to set-up and maintain when used alone in remote healthcare centers, portable mobile units, or in specialty homes.

SUMMARY

A need of invention exists for systems and methods to address the aforementioned problems as well as other problems associated with bio potential recordings. Disclosed herein are affordable low-cost systems with easy access to 'diagnostic' quality monitoring that is reproducible, repeatable and enables easy follow-up prognosis to be administered at local points-of-interest (such as, but not limited to, ATM-like Kiosks at Walgreens®, Walmart®, etc.), specialty/elderly homes, or population-level medical tests required in emergencies and battlefield triages. Embodiments of the invention provide the "right care at the right time in the right way" and reduce the burden on emergency healthcare infrastructure, thereby freeing up critical resources. Further embodiments apply readily to wearable gear enabling the patient to monitor vital signs continuously over long-periods of time.

According to an aspect of some embodiments, a non-contact method for monitoring bio-signals (such as vital-signs) in a subject is provided, the method comprising: collecting one or more sets of data from at least one electrode coupled to respective locations on a flexible textile material worn by the subject; processing the data to provide features from monitored signals and compare the features with reference signals substantially close to the point of the acquired data; and analyzing the data to identify at least one of short-term and long-term trends of changes in bio-signals (e.g., vital signs), the analysis selected from at least one of medical image analysis, motion artifact correction, mathematical algorithms, and statistical algorithms.

According to another aspect of some embodiments, a non-contact sensor is provided comprising: one or more electrodes coupled to respective locations of a flexible textile material worn on a body, a low power multi-channel electronic chip coupled to the textile-attached electrodes; and a processing unit coupled to the electronic chip to identify at least one of short-term and long-term trends of changes in bio-signals, the analyzing selected from at least one of medical image analysis, motion artifact correction, mathematical algorithms, and statistical algorithms.

According to yet another aspect of some embodiments, exemplary methods and systems are disclosed that provide self-automated, self-operable placement of electrodes on textile for bio-signal monitoring, such as, but not limited to, electrocardiograms (ECG), electroencephalograms (EEG), electrocardiogram (ECG), electromyogram (EMG), electrooculography (EOG), galvanic skin response (GSR), muscle activity, etc., requiring no medical assistance.

According to another aspect of some embodiments, wireless monitoring devices are disclosed herein using for example, radio frequency transmission to significantly improve the speed and convenience of medical diagnostics.

Recent technological advances in wireless health monitoring have opened new avenues in medical healthcare improving the quality of life and enabling research into deeper areas of human body. Combined with appropriate data and signal infrastructure, the wireless monitoring devices disclosed herein using for example, optical image processing, flexible circuits and low-power multi-channel sensor design, significantly improves the speed, longevity, and accuracy of medical diagnostics leading the way towards a healthier society.

Methods and devices disclosed herein may have one or more of the following aspects: require no dedicated medical resource, generate diagnostic quality results, provide for motion artifact correction, does not induce discomfort or irritation, and enables long term recording.

In addition, an exemplary system and method disclosed herein provides for a up to a 12-lead wireless ECG design using non-contact sensors that includes a novel combination of analog signal processing along with optical signal processing to achieve the required accuracy of which disseminates diagnostic information and is also useful for effective critical care practices in pediatrics. Advantageous features may include:

- no 'prepping' or a dedicated medical resource,
- diagnostic quality 12-lead ECG suitable for long-term diagnosis and follow up,
- motion artifact correction in standing posture,
- noncontact sensors without upper body exposure,
- position of sensors accurately adjusted by using a real time 3D perspective with positional errors less than ±1 cm,
- instant recording and signal transmission to specialized remote centers,
- available at local points-of-interest as mentioned above, and
- significantly cheaper and affordable as compared to current solutions.

Non-contact sensors and sensor techniques disclosed herein can be used in children, eliminating the use of wet/gel electrodes that not only require technical assistance but also cause skin irritation due to metallic allergies and rashes, in particular in infant patients. Some embodiments herein use motion artifact correction along with a unipolar ECG lead system to enhance the accuracy of recorded electrogram (e.g., ECG) tracings. The electronic sensors are coupled with flexible electrodes which are placed on a stretchable belt worn easily with minimal assistance. The electronic sensors combine data from multiple electrodes and transmit the data wirelessly to a remote clinic for continuous long-term monitoring.

Some embodiments herein utilize novel flexible circuits and sensors interfaces and optical imaging techniques. According to a further aspect of some embodiments, low power non-contact sensors are provided that are configured with flexible form-factors to ensure that the device is not obvious and easy to wear even when a subject wears several (e.g., 10 electrodes, in the case of a 12 lead ECG).

DETAILED DESCRIPTION

Figure 1A:
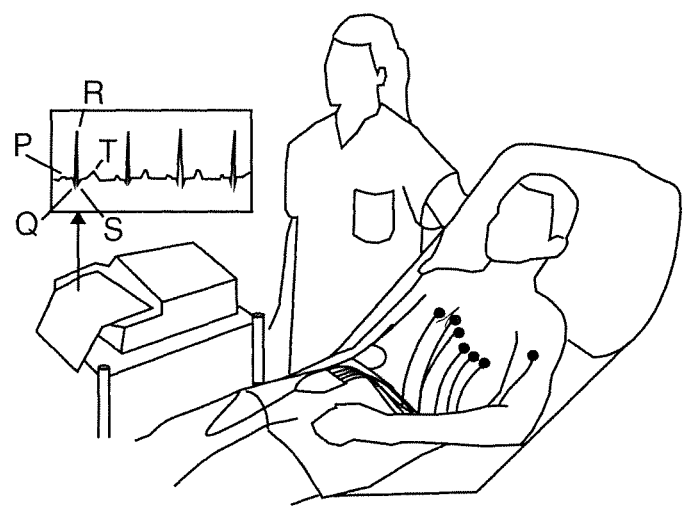
FIG. 1A shows a conventional ECG equipment setup performed with a patient in a supine position and with upper body exposure. A medical professional administers and oversees the setup and data collection.

In the description herein, it is understood that a word appearing in the singular may encompass its plural counterpart, and a word appearing in the plural may encompass its singular counterpart, unless implicitly or explicitly understood or stated otherwise. Furthermore, it is understood that for any given component or embodiment described herein, any of the possible alternatives listed for that component may be used individually or in combination with one another, unless implicitly or explicitly understood or stated otherwise. It is to be noted that as used herein, the term "adjacent" can imply but does not inherently require immediate adjacency. Moreover, it is to be appreciated that the figures, as shown herein, are not necessarily drawn to scale. Some of the elements may be drawn merely for clarity of illustration or may be excluded for clarity of illustration. Also, reference numerals may be repeated among the various figures to show corresponding or analogous elements. Additionally, it will be understood that any list of such alternatives is merely illustrative, not limiting, unless implicitly or explicitly understood or stated otherwise. In addition, unless otherwise indicated, numbers expressing quantities of constituents or conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

As used herein, the terms "positioning" and "placement" are interchangeable unless the context makes clear otherwise. Both terms imply that an object, such as a sensor, is being arranged at a well-defined or definable position (e.g., with coordinates in two- or three-dimensional space), usually defined according to an anatomical frame of reference.

FIG. 1A shows a conventional ECG procedure. The procedure is often performed with the subject (e.g., a patient) in a supine position. Wired contact electrodes are attached to the chest, upper arms, and legs. To reach these areas the subject's upper body is exposed. The detected signals are transmitted via wires to dedicated recording equipment or a general purpose computer for recordation and, optionally, digital processing. A nurse or other medical practitioner determines the positions for the electrodes on the patient when setting up the recording equipment. While the recording is in progress, the patient must remain still in the supine position.

Heart rate is considered a primary vital sign for cardiovascular disease examinations. ECGs provide heart rate as well as other measurements suited for inpatient/outpatient care. Modern ECG is derived from the Einthoven-Wilson model where a number of "differential" scalar quantities are measured by unipolar chest leads and bipolar limb leads (precordial). Major amplitude deflections of the ECG signals are labeled with the letters P, Q, R, S, T and U; a well-defined phase of cardiac activity is associated with each of these deflections. The deflections mark the link between the electromagnetic and the mechanical activity of the heart.

Figure 1B:
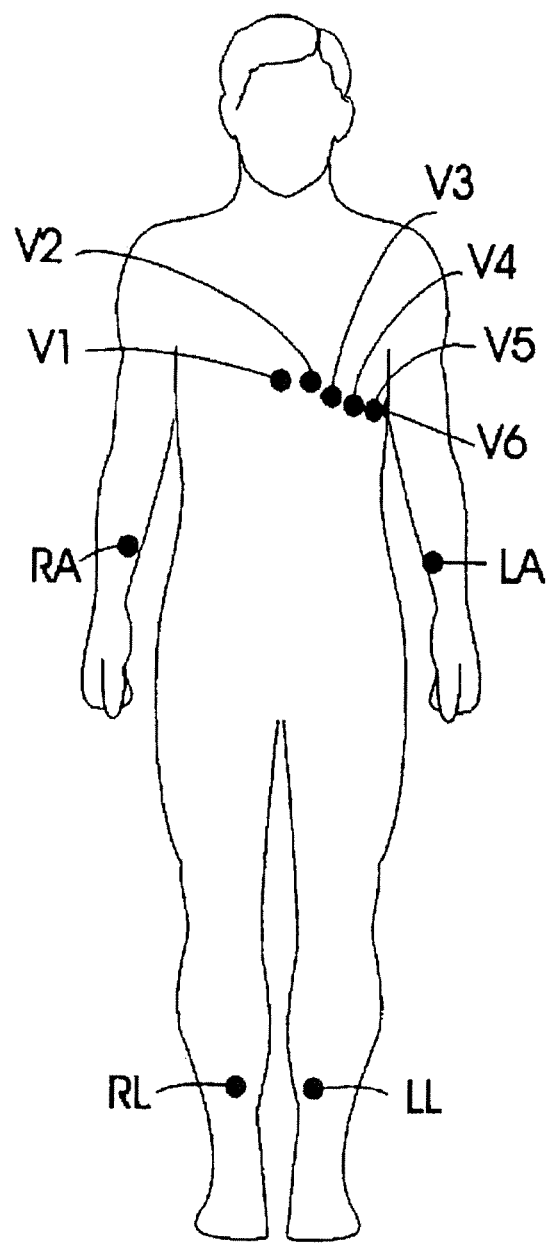
FIG. 1B shows the traditional 10 electrode positions for a 12 lead electrocardiogram with respect to an adult frame.

FIG. 1B shows the 10 electrode positions typical for a 12-lead conventional procedure. In the conventional Einthoven-Wilson model, the necessary grounding and signal return are fixed to the subject's right leg, anatomically the most distant part from the human heart potential. The 12-lead ECG is the norm in the modern medical use. However, embodiments may also be configured with as few as 2 up to at least 12 leads, depending on the desired application. Fewer electrodes/leads has advantages such as ease of implementation (e.g., owing to less hardware) but typically at a cost of reduced amount and/or quality of the collected data. A 12-lead configuration of traditional method is labeled as golden reference in medicine to date. The new wearable devices must thus be capable to trace 12 leads along with six unipotential chest leads for accurate diagnosis to conform to the golden reference.

Figures 2A, 2B, 2C, 2D, 2E:
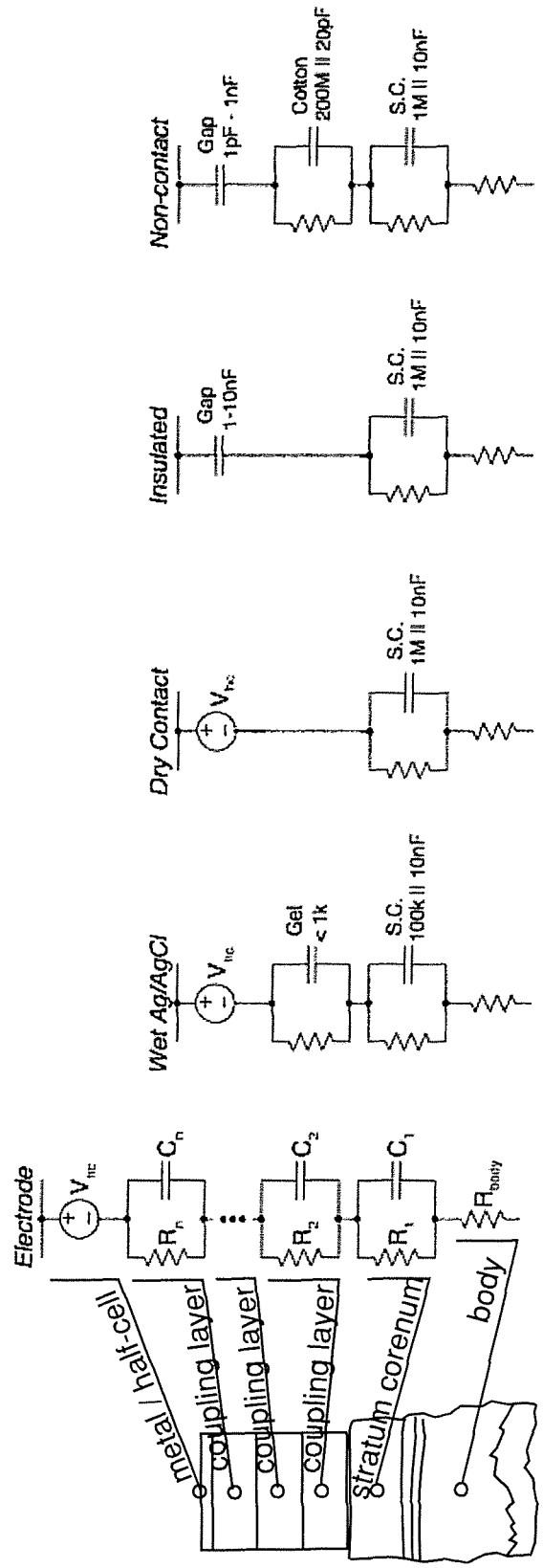
FIGS. 2A to 2E show schematics of different electrode types.

FIGS. 2A-2E provide an overview of different types of electrodes. The two main categories are contact electrodes (FIGS. 2A-2D) and non-contact electrodes (FIG. 2E).

FIG. 2A illustrates pictorially and schematically a generic contact electrode. At a minimum, a contact electrode includes a half cell with an associated potential, $V_{hc}$. One or more coupling layers may be provided which are interposed between the metal of the electrode and the stratum corneum (the outermost layer of the epidermis, abbreviated as S.C. in the figures). Dry epidermis presents very high impedances which can inhibit effective recording from contact electrodes.

FIG. 2B shows a standard wet Ag/AgCl electrode with a coupling layer consisting of an electrolytic gel. The gel improves the contact between the epidermis and the metal, reducing the contact impedance as well as motion artifacts. The gel is commonly applied to the electrode just before the electrode is applied to the patient's skin. Frequently medical practitioners will also clean and abrade the stratum corneum to further improve the contact surfaces prior to placing the sensor and gel. In practice, a wet electrode usually includes a foam perimeter with an adhesive that holds the electrode to the patient's skin during use.

Despite being the default industry standard, wet electrodes have several drawbacks. They tend to be uncomfortable to patients, especially when attached for extended periods of time. The relatively involved prep required (e.g., abrading the skin, applying the electrolytic gel, etc.) means wet electrodes are primarily used by medical professionals and are unavailable for patients to use outside of a hospital or clinical setting. The skin preparation causes irritation/hypodermal sensitivity for many subjects. Persons with skin allergies sometimes have reactions. Moreover, many patients are apprehensive towards hospitals and "white coat" doctors—this apprehension can extend to wet electrodes owing to their omnipresence in hospitals and similar healthcare facilities. In addition, wet electrodes, like other contact electrodes, are susceptible to introducing signal artifacts from muscular contractions. Biopotential recordings like ECG are frequently monitored by expert technicians at all times to ensure sources of signal artifacts and disruptions are kept to a minimum.

FIG. 2C shows a dry electrode. In a dry electrode, no electrolytic gel is provided. Dry electrodes are generally regarded as easier to use than wet electrodes, but at the cost of greater impedances and decrease in signal to noise ratio.

FIG. 2D shows an insulated electrode. In contrast to a dry electrode, a small gap exists between the metal plate of the electrode and the epidermis. The gap exists only between the metal plate of the electrode and the epidermis. An insulated electrode is made up of a conductive metal surrounded by an adhesive material. Suction electrodes are also a type of insulated electrode.

FIG. 2E shows a non-contact electrode. Non-contact electrodes are frequently positioned on the outside of an article of clothing. The clothing material varies, with fabrics such as cotton providing greater user comfort and other fabrics such as nylon providing greater conformity to the skin surface and reducing motion artifacts associated with movement of the fabric relative to the skin. No explicit electrolyte is used for non-contact electrodes. Because the electrodes can be fixed to apparel, there is no need to expose a subject's body. An active circuit may be used to enhance signal strength. Challenges associated with non-contact electrodes include the need for a separate power source and high sensitivity to motion artifacts.

Figure 3:
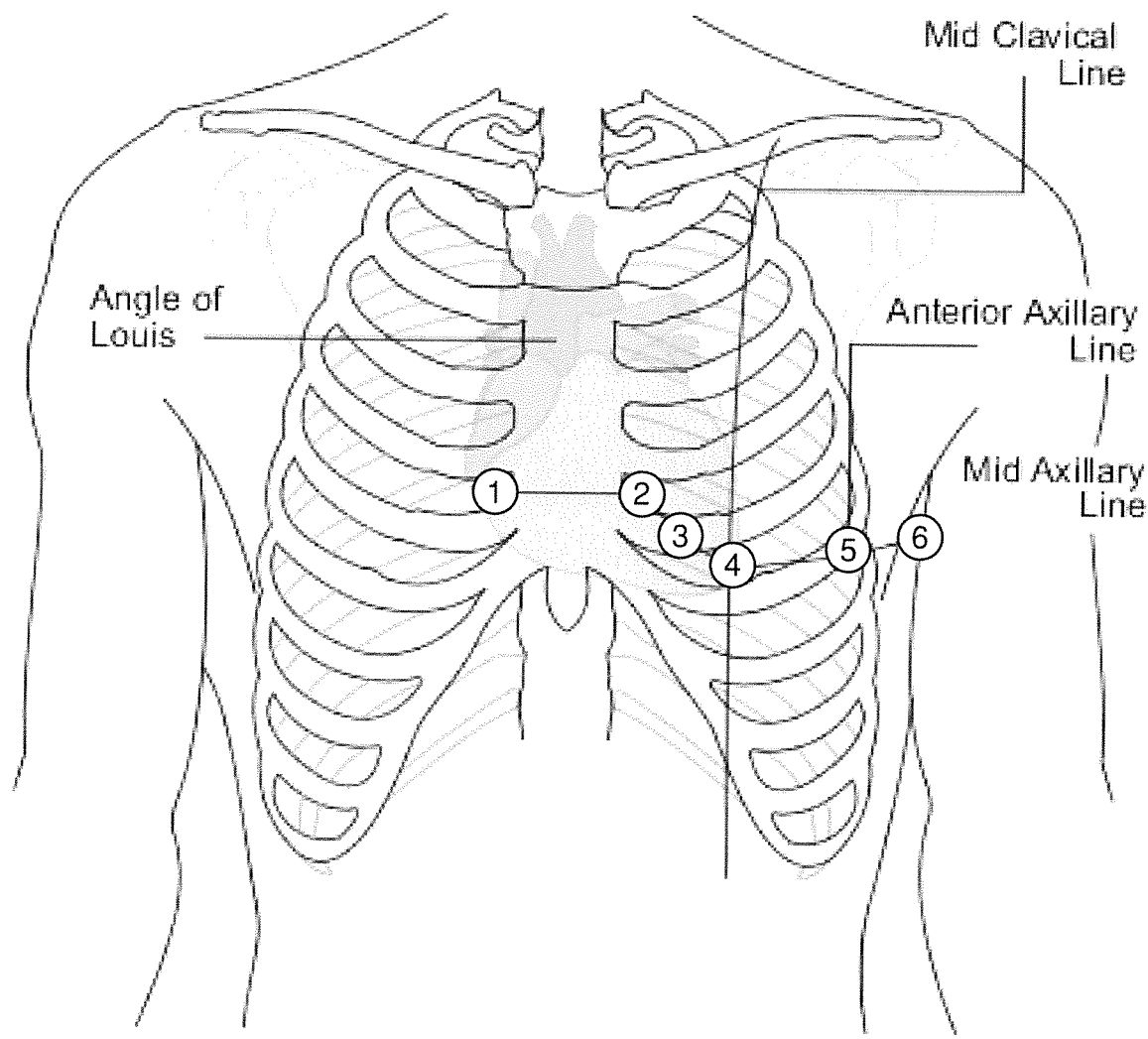
FIG. 3 shows an enlarged view of the thorax region of an adult patient with electrode positions V1 to V6 indicated for a 12 lead electrocardiogram.

FIG. 3 shows an enlarged representation of a generic adult thorax with the positions of six electrodes for an ECG. These positions are commonly referred to as V1 through V6. The figure illustrates the optimal positions of the electrodes, and Table 1 below describes the illustrated positions in words. The accuracy of the positions V1-V6 with respect to a subject's anatomy is particularly important and one of the greatest sources of potential error on the part of the individual placing the electrodes (e.g., a medical professional or the subject himself/herself). The remaining four electrodes not shown in Table 1 that would typically be used for a 12 lead ECG configuration are RA (right arm), LA (left arm), LL (left leg), and RL (right leg).

TABLE 1

Electrode Positions.

| Position of chest electrodes | Anatomical position for placing chest electrodes |
| --- | --- |
| V1 | Right $4^{th}$ intercostal space at Rt parasternal margin |
| V2 | Left $4^{th}$ intercostal space at Lt parasternal margin |
| V3 | Mid way between 2nd and 4th electrode |
| V4 | $5^{th}$ intercostal space at mid clavicular line |
| V5 | $5^{th}$ intercostal space at anterior axillary line |
| V6 | $5^{th}$ intercostal space at mid axillary line |

Despite training of medical professionals in the setup of ECG recordings and, particularly, in placement of unipolar chest electrodes, substantial positioning discrepancies can happen even for the same patient that may lead to wrong diagnosis especially when determining symptoms for myocardial ischemia and infarctions. Similarly, errors can occur while taking longitudinal data spread across time. These errors are termed as inter- and intra-operable errors respectively. The accuracy of the positions of the electrodes can critically impact the quality of measured signals and the medical information gleaned from the signal data. Inconsistency in electrode placement causes differences between two sets of signal data where the differences can be wrongfully attributed to a physiological change in the patient. Hence, there is a need for identical repeatable and reproducible placement of these unipolar chest electrodes for accurate diagnosis. In short, variability in electrode position (between two or more recordings) and error in electrode position (for any one recording) risk compromising fidelity and accuracy of the bio-signal recordings. The impacts of these risks can in some cases be severe, such as with a misdiagnosis and subsequent mistreatment of a patient based on ECG artifacts attributed to a physiological condition when in fact they are caused by poor or improper electrode positioning.

The negative consequences of sensor position errors and sensor position variability discussed in the preceding paragraph are amplified for non-contact electrodes as compared to conventional contact electrodes which are placed directly on a patient's skin. The physical misplacement of just a few centimeters in the case of non-contact electrodes can result in as much as a 10-20% increase in a signal's error as compared to the case of contact electrodes. This is another challenge and a factor which has hampered the adoption and widespread use of non-contact electrodes.

Figure 4:
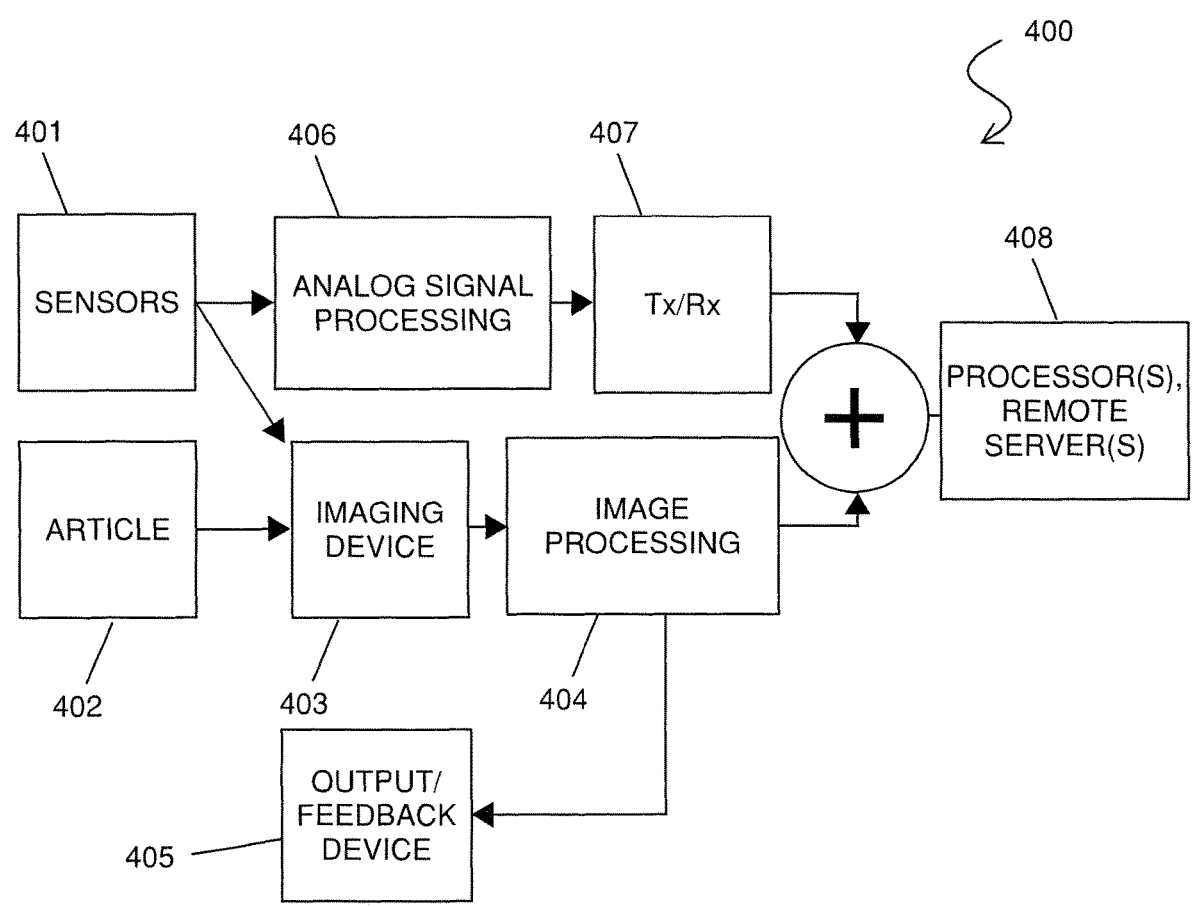
FIG. 4 is a block diagram for an example bio-signal monitoring system that includes assisted sensor placement.

FIG. 4 is a block diagram consistent with some exemplary embodiments herein which utilize a novel approach of optical image processing with biopotential signal processing to achieve an improved, highly accurate, and low cost system 400 for bio-signal monitoring setup and recording (e.g., for a 12-lead ECG). The systems and methods summarized by FIG. 4 are especially well suited for bio-signal recordings using non-contact sensors, in particular wireless non-contact electrodes. However, the disclosed systems and methods are suitable for implementation with virtually any bio-signal recording electrode, be it a known type (wet, dry, insulated, etc.) or developed in the future.

The exemplary system configuration represented by FIG. 4 enables bio-signal recordings to be collected from, for example, a fully clothed human even while the subject is in a standing posture, in a friendly environment, and without technical assistance. Moreover, the systems can be self-operable, fully or partially automated. Applications using the methods and systems herein include, but are not limited to, electroencephalograms (EEG), electrocardiograms (ECG), electromyograms (EMG), electrooculograms (EOG), and galvanic skin response (GSR).

The representative system 400 for bio-signal monitoring includes a plurality of sensors 401 which are fixable to an article 401 worn by a subject (e.g., an old patient, a child patient, a neonatal patient, etc. with minimal assistance). As used herein, the terms "subject" and "patient" are interchangeable. Both terms refer to an individual from whom a bio-signal (e.g., one or more biopotentials) is to be measured and recorded, regardless of the location of the individual (e.g., hospital, clinic, home, point-of-interest, etc.). Certain features are desirable for the article 402 worn by the subject, such as conformity to the subject's body. An imaging device 403 is positioned at a distance of, for example, one and half meter from the subject and is configured to capture a real time colored 3D perspective (e.g., a single image or a series of images such as a video) of the subject. Procedurally, this involves the imaging device being arranged in a space at a height approximately 39 inches from earth surface tilted by an angle of 15-20° upwards, conducive for the individual to be positioned in the field of view of the imaging device. It is preferable although not necessary in all instances that the imaging device 403 have a field of view that includes all of the target sensor positions. Target sensor positions are specific positions with respect to the subject's anatomy that are optimal for detecting a biosignal (e.g., biopotential) for a recording such as an ECG. As already discussed above, in the case of a 12-lead ECG, six of the target sensor positions are V1 through V6, all of which are along the subject's chest/thorax. Block 404 is representative of optical image processing or, structurally speaking, one or more processors (and their accompanying hardware such as power supply, etc.) that execute computer-readable instructions to perform the optical image processing. Specifics of optical image processing 404 are provided below in connection with FIGS. 5, 6A-6D, and 7A-7B. In brief, the image data from the imaging device 403 is used to determine target sensor positions that are specific to the subject. For the example case of an ECG, V1 through V6 are descriptively consistent with Table 1 above. In practice, however, subject bodies exhibit substantial variability. Therefore, the specific positions (e.g., expressed in spatial coordinates or the like) of V1 through V6 for a specific subject must be determined. In some exemplary embodiments, the actual sensor positions are also determined from the image data supplied by the imaging device 403. The optical image processing processor (s) 404 compare the target sensor positions with the actual sensor positions, and the result of the comparison are provided to the subject as feedback via an output device 405.

An exemplary output device 405 is a monitor or screen, for example. Other alternative output devices that can be used in place or in addition to a monitor or screen include a projector, one or more speakers, or one or more tactile feedback devices. In other words, the results of the comparison can be provided as any of one or more of visual, auditory, and tactile forms of feedback. While visual feedback is preferred for its ease of understanding, some embodiments may be tailored to the visually impaired, and therefore visual feedback is supplemented or substituted with auditory and/or tactile feedback. Auditory feedback is useful for circumstances when a subject is not maintaining eye contact with a visual output device 405 such as a screen. A projector can be used to project visual feedback onto the subject's clothing.

For assisted sensor placement for bio-signal monitoring, sensors 401, imaging device 403, optical image processing processor(s) 404, and output device 405 constitute base hardware, assuming a suitable article of clothing is worn by the subject. The remaining elements of system 400 shown in FIG. 4 will be discussed below, but first exemplary aspects of the optical image processing 404 will be disclosed.

Figure 5:
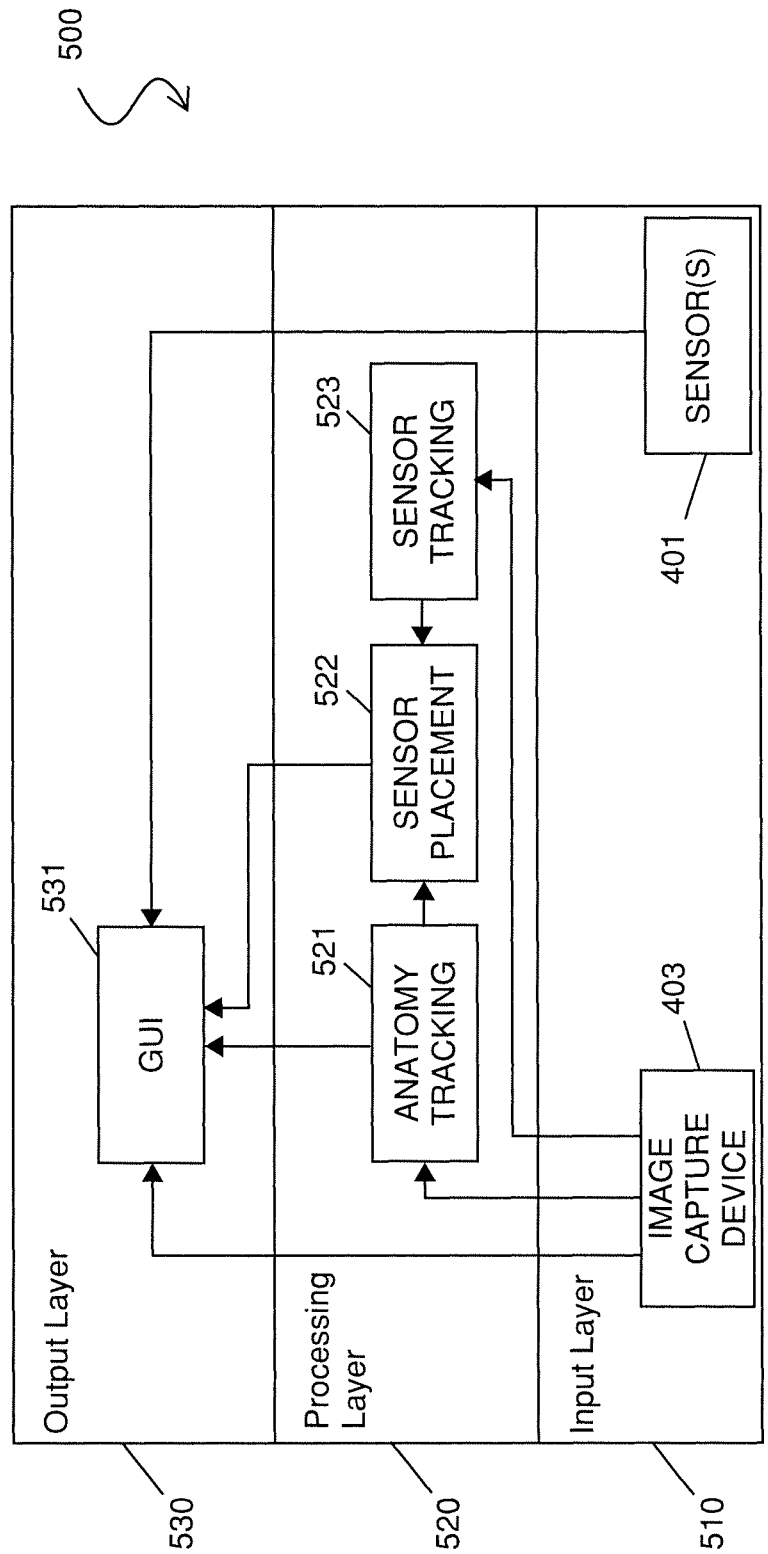
FIG. 5 is a schematic for a system providing assisted sensor placement for bio-signal monitoring.

FIG. 5 is a block diagram which provides a general breakdown for the optical image processing block 404 of FIG. 4. The overall system 500 for assisted sensor placement for bio-signal monitoring is represented for illustrative purposes as three distinguishable layers: an input layer 510, a processing layer 520, and an output layer 530.

The input layer 510 of FIG. 5 includes the imaging device 403 and sensors 401. An exemplary imaging device 403 comprises a plurality of cameras and one or more processors configured to detect depth (e.g., based on a combination of two-dimensional images captured from different orientations with respect to the subject). A suitable commercially available imaging device meeting this description is a Microsoft® Kinect® device. Although a primary consumer application of Microsoft® Kinect® is video games, Microsoft® Kinect® is also popular among medical professionals and researchers for human anatomical studies and applications. At a minimum, a single imaging device 403 is included in the input layer 510. However, multiple imaging devices 403 (e.g., Multiple Microsoft® Kinect® sensors) can be used together to capture the entire body of a subject, for example. The imaging device 403 is a type of optical position sensor. The imaging device 403 may include miniaturized 3D image sensors on silicon for ascertaining the position/depth of bio-signal recording sensors on the human body. Such configurations aid in precise positioning of the non-contact sensors and increase the diagnosis accuracy of the bio-signal recording.

The output layer 530 typically includes a display, screen, or other visual output device for displaying a graphical user interface (GUI) 531 to the subject. The subject may use a touch interface to assist in positioning the sensors in the desired location. Another useful verification is the image alignment applicable for different biometric shapes. In some exemplary embodiments, the GUI and/or other feedback mechanisms are provided to the subject in order for the system to be self-operable. That is to say, the individual in need of the ECG (or other bio-signal monitoring) is positioning the sensors on himself/herself without any assistance. However, in alternative implementations, the disclosed system additionally or instead provides the feedback to a caretaker or medical professional who is assisting the subject. This is particularly desirable for elderly persons or infants, including prenatal subjects, who are not of adequate mind and/or body to carry out the self-operable procedures described herein. Indeed, embodiments of the invention are useful in improving accuracy and precision of sensor placement for any user, regardless of whether that user is placing sensors on himself/herself or is a medical professional such as a doctor, nurse, or technician placing sensors on a patient under his or her care.

The processing layer 520 of FIG. 5 is characterized by three processing blocks: anatomy tracking 521, sensor tracking 523, and sensor placement 522. Anatomy tracking 521 is described in detail in FIG. 6A. Sensor tracking 523 is described in detail in FIGS. 6B and 6C. Sensor placement 522 is described in detail in FIG. 6D.

Figure 6A:
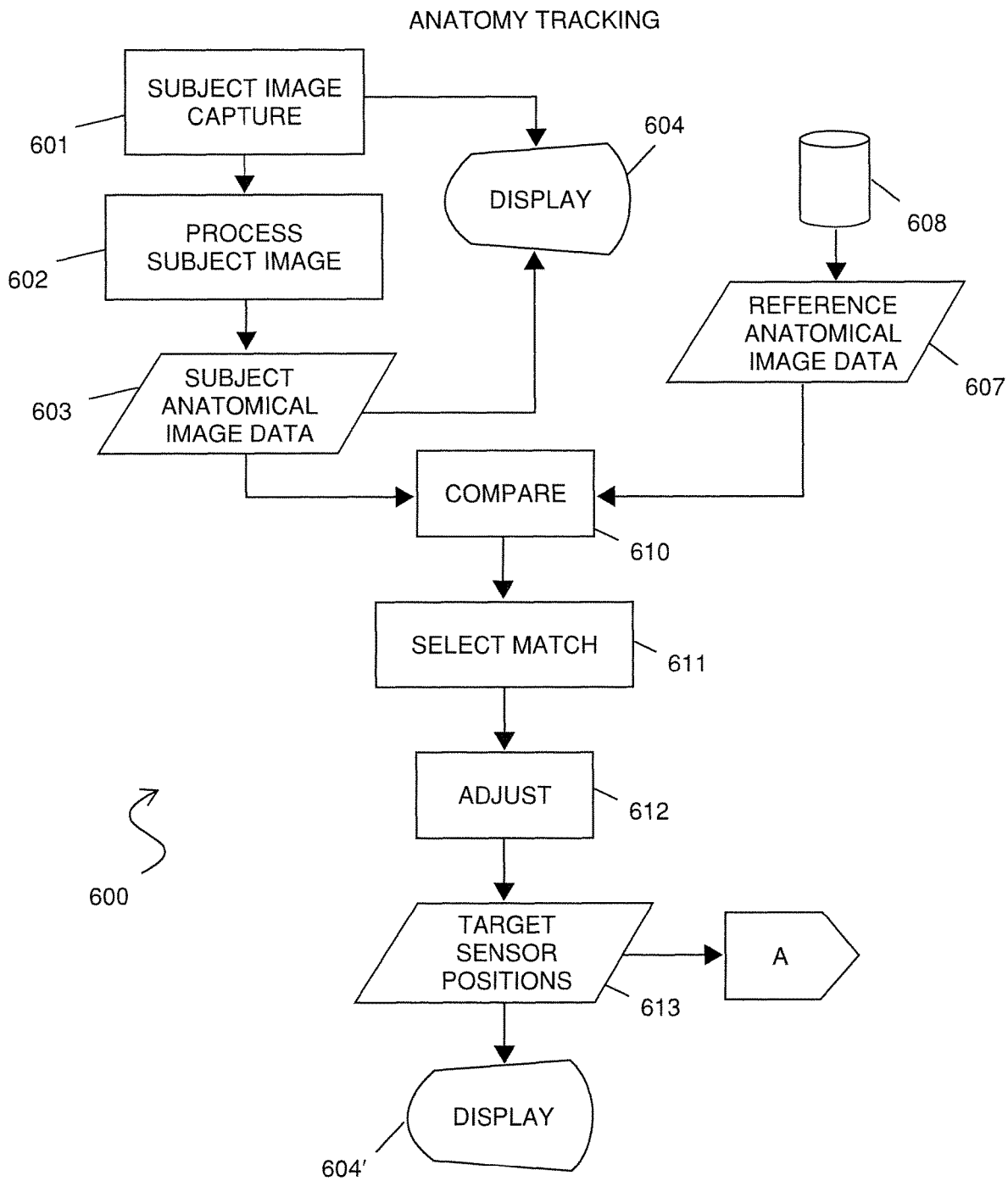
FIG. 6A is a flowchart of an exemplary procedure for anatomy tracking.

FIG. 6A shows an exemplary process 600 for anatomy tracking 521 (FIG. 5) of a subject. Process 600 serves a primary purpose of determining target sensor positions on a subject (specifically on an article worn by a subject) based on the subject's unique anatomy. Human have widely variable anatomical parameter values and characteristics. Height, weight, age, skeletal structure, posture, and relative body part proportions, among other traits, affect the precise positions for bio-signal sensors. For an ECG, the precise coordinates (e.g., in three-dimensional space) of positions V1 through V6 are subject-specific. That is to say, the spatial coordinates differ from one subject to another. Process 600 allows for determining target sensor positions that are specific to any subject using the system (e.g., the system 400 of FIG. 4). An image (e.g., series of images forming a video) of the subject is first captured (block 601). Either custom or off the shelf image-processing routines are adequate for providing initial processing 602 of the captured image to identify the positions of the subject's primary anatomical reference points. For instance, anatomical reference points are generated at block 602 for the left shoulder, right shoulder, left hip, and right hip. Additional or alternative references points may be used in variations on this example, as will be evident to those of skill in the art. The shoulders and hips are in any case reliable and standard reference anatomical reference points. Processing 602 generates positions/coordinates of subject anatomical image data. The term "subject anatomical image data" implies i) that the data describes one or more aspects of the subject's anatomy such as the position of each shoulder and each hip, and ii) that the data is tied to the original captured image. In particular, subject anatomical image data permits the indication of the selected anatomical reference points as indicia superimposed on a reproduction of the original captured image. This is represented in FIG. 6A by arrows from blocks 601 and 603 to display block 604. As visual feedback, the system's feedback device (405 in FIG. 4) displays on a screen the subject's own image with indicia superimposed thereon showing the anatomical reference points. This can be achieved with, for example, dots at the center of each of the subject's shoulders and hips.

Displaying a reproduction of the original captured image and the subject anatomical reference data 603 is exemplary, and some embodiments may display alternative features. For instance, if a projector is used to project visual feedback directly onto the subject, a reproduction of the subject's original image is not necessary. The subject anatomical image data for the anatomical reference points can simply be projected onto the user. For instance, the projector would project circles or cross hairs onto the center of each of the subject's shoulders and hips. This technique can be used for any feedback indicia.

The image-processing algorithms utilized at block 602 improve the image capture device accuracy (e.g., Kinect® sensor accuracy) especially for resource-constrained systems to beneficially improve cost. The image processing provides anatomy detection and localization. Conventional approaches for medical image analysis use marginal space learning (MSL) and can be incorporated at block 602. MSL is useful in practice as it localizes a single object. However, some exemplary embodiments may use multiple classifier stages to detect the position of the object. For example, to detect a hearts location, there are three sets of classifiers, one each for translation, translation and rotation, translation rotation and scaling respectively. If these classifiers are applied to 10 ribs in the human thorax, it will take 10×3=30 different classifiers to identify and detect the heart location.

In comparison, a single regressor forest may be performed between boosting, regression forests, and cascades for resource-constrained anatomical systems.

In continued reference to FIG. 6A, in order to identify the target sensor positions (e.g., for V1 through V6 for an ECG) specific to the subject, reference anatomical image data 607 is retrieved from a database 608 on a computer-readable storage medium. The reference anatomical image data includes a plurality of data sets from a large sample of subjects. Each reference data set describes with specificity target sensor positions for a specific subject's anatomy together with the positions of the anatomical reference points for that same subject. A comparison 610 is made between the immediate subject's anatomical image data 603 and the reference anatomical image data 607, and the closest match is selected (block 611). The closest matching reference data—which includes the relative positions of both anatomical reference points and target sensor positions for the reference subject's anatomy—is then adjusted (block 612) to scale to the immediate subject's anatomical image data. The following data is known: the precise positions of the anatomical reference points for the immediate subject; the precise positions of the anatomical reference points for the reference data subject; the precise target sensor positions for the reference data subject. From these known data, geometric scaling allows simple determination of the target sensor positions 613 for the immediate subject. Target sensor positions 613 are provided as feedback displayed to the subject (block 604').

An exemplary visual feedback for the subject is a reproduction of the original captured image from block 601 with indicia for the target sensor positions 613 (e.g., with shapes, cross-hairs, color spots, or other indicia) superimposed thereon. This feedback is easily displayed on any screen such as a computer monitor, tablet screen, or smartphone display. Alternatively, target sensor positions 613 may be displayed without the reproduction of the subject's image, such as in the case of a projector projecting the target sensor positions directly onto the user. For circumstances in which the subject is assisted by a separate user, the displayed information at 604 and 604' is displayed to the separate user instead of or in addition to the subject.

The reference data stored in database(s) 608 may be collected or obtained from a wide variety of sources. Reference subjects may be real humans or, alternatively, may be exemplary virtual subjects generated based on averaged data from a large collection of real world subjects. Reference anatomy data is obtainable by many different forms of optical imaging used in medicine. Computerized tomography (CT) data and magnetic resonance imaging (MRI) data, among others, may be used. Existing private and/or public databases may also be used, such as, for example, the Korean Human Dataset available online. The Korean Human Dataset provides two distinct data sets, one each for male subjects and female subjects. Separate databases 608 may be maintained online to allow the system to be used as an online tool from a variety of locations.

While not explicitly represented in FIG. 6A, the procedure 600 preferably includes a loop which provides adjustment of the displayed target sensor positions if the subject moves. For example, if the subject moves 6 inches to the left, any indicia of the subject's anatomical reference points and/or target sensor positions are similarly shifted to remain accurate in reference to the subject's real-time body position. In this respect the subject's image capture at block 601 is likened to a video capture as opposed to a still shot. It should be appreciated that the expression of "an image" as used herein can refer to either a singular still shot or to a series of consecutive shots that together yield a motion picture or video.

Figure 7A:
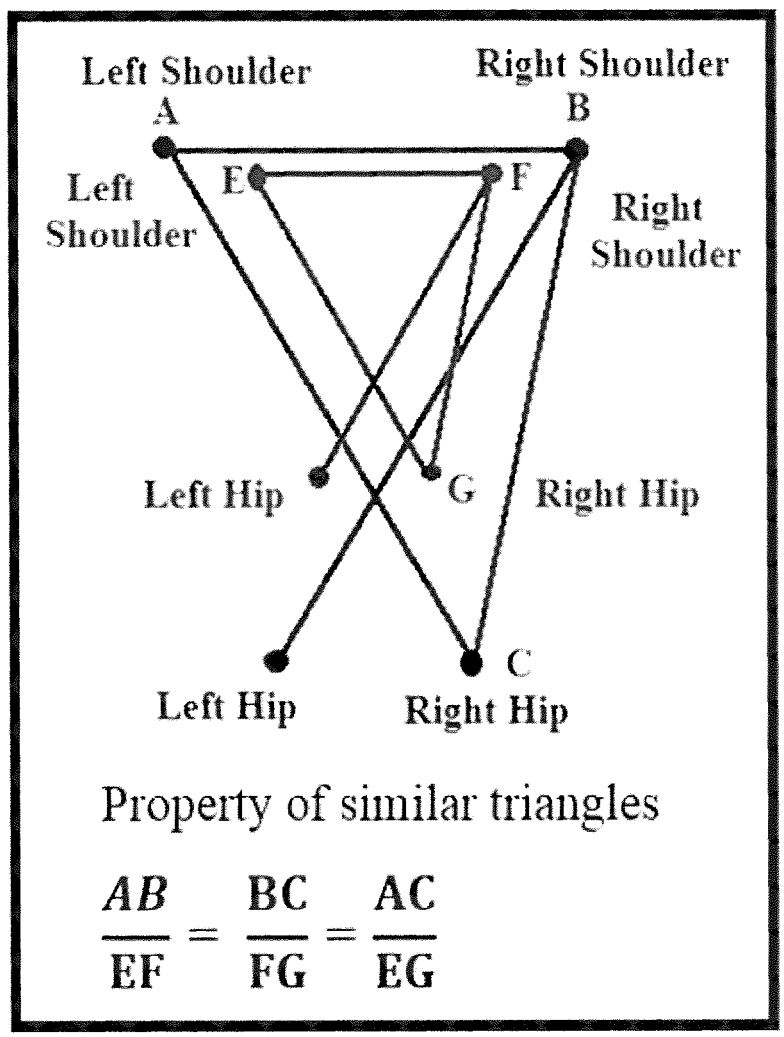
FIG. 7A is a diagram illustrating the geometry and biometrics involved in matching new subject data with reference data.

FIG. 7A illustrates biometric geometry involved in the comparison and match selection blocks 610 and 611 of FIG. 6A. As an exemplary but non-limiting approach, the best match is selected using the property of similar triangles, comparing the current/immediate subject's biometrics to the stored reference biometrics. In FIG. 7A, points A, B, and C represent anatomical reference points of a reference data set. Points E, F, and G represent anatomical reference points of the immediate subject (e.g., the user). Each side of the triangle ABC is given its own score relative to how closely it matches the corresponding side of the triangle EFG. Each side is then weighted based on its importance. Weighting can be customized to attribute greater influence to some biometrics over other different biometrics. In this example, the three biometrics in consideration are the following distances: left shoulder to right shoulder, left shoulder to right hip, right shoulder to right hip, and right shoulder to left hip. Additional and/or alternative biometrics may be used in other embodiments and implementations. The reference data set with the lowest cumulative score is selected as the best fit for matching with the current subject.

Figure 7B:
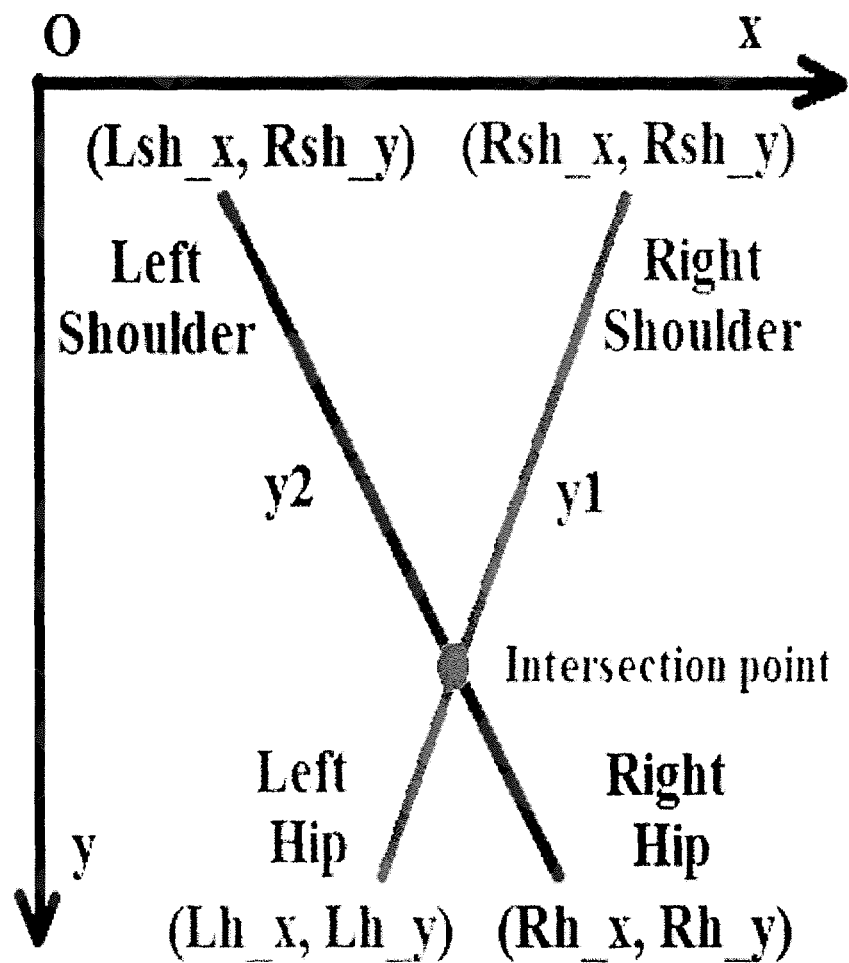
FIG. 7B is a diagram illustrating the geometry and biometrics involved in determining target sensor locations.

FIG. 7B illustrates biometric geometry involved in the adjustment block 612 of FIG. 6A that yields the target sensor positions for a given subject based on the best matching reference data. The reference biometrics and points are stretched (e.g., enlarged or reduced) using the i) distance between the left and right shoulders and ii) the distance between the shoulder points and the intersection of two lines drawn from each shoulder to the opposite hip. That is to say, the first line connects the left shoulder and the right hip, and the second line connects the right should and the left hip, as illustrated in FIG. 7B. The scaled enlargement or reduction of the geometry yields target sensor positions specific to the immediate subject based on the known target sensor positions of the reference data. Alternative approaches to mapping the reference data to the current subject's anatomical image data may also be used.

Figure 6B:
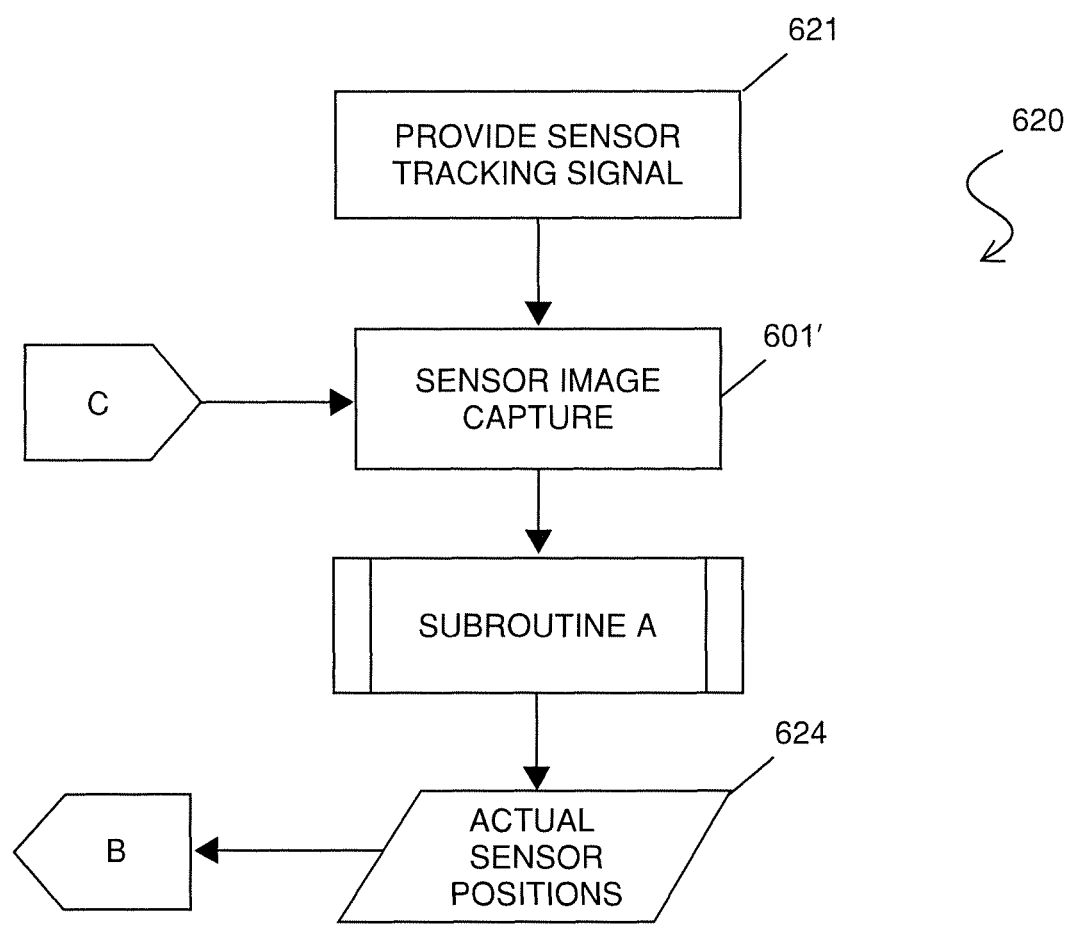
FIG. 6B is a flowchart of an exemplary procedure for sensor tracking.

FIG. 6B shows an exemplary process 620 for sensor tracking 523 (FIG. 5). As an exemplary low cost configuration, the initial input data is the same as for anatomy tracking process 600—namely, an image (i.e., image data) captured by an image capture device. This is shown in FIG. 6B at block 601' and corresponds with block 601 in FIG. 6A. From the initial image data, subroutine A provides image analysis to determine the actual sensor positions 624. It is advantageous for the actual sensor position data 624 to use the same frame of reference (e.g., the subject's anatomy) as the target sensor position data 613 for ease of comparison. However, a unitary frame of reference is not strictly necessary so long as provision is made for translating points from one frame of reference to the other, thereby facilitating comparison. Actual sensor positions are the positions (e.g., coordinates in two- or three-dimensional space) of the sensors (e.g., non-contact electrodes) in substantially real time. In order for image analysis subroutine A to accurately differentiate parts of the captured image that are sensor from parts of the image that are not sensors (e.g., clothing, skin, environmental structures and surfaces near the subject, etc.), it is advantageous to provide unique electromagnetic signatures for the sensors which are not expected from any element in the captured image except for the sensors (block 621). As an example, each sensor may have affixed thereto or incorporated therein a light emitting diode (LED) that provides a small circle of light on the subject that contrasts with its surroundings.

Figure 6C:
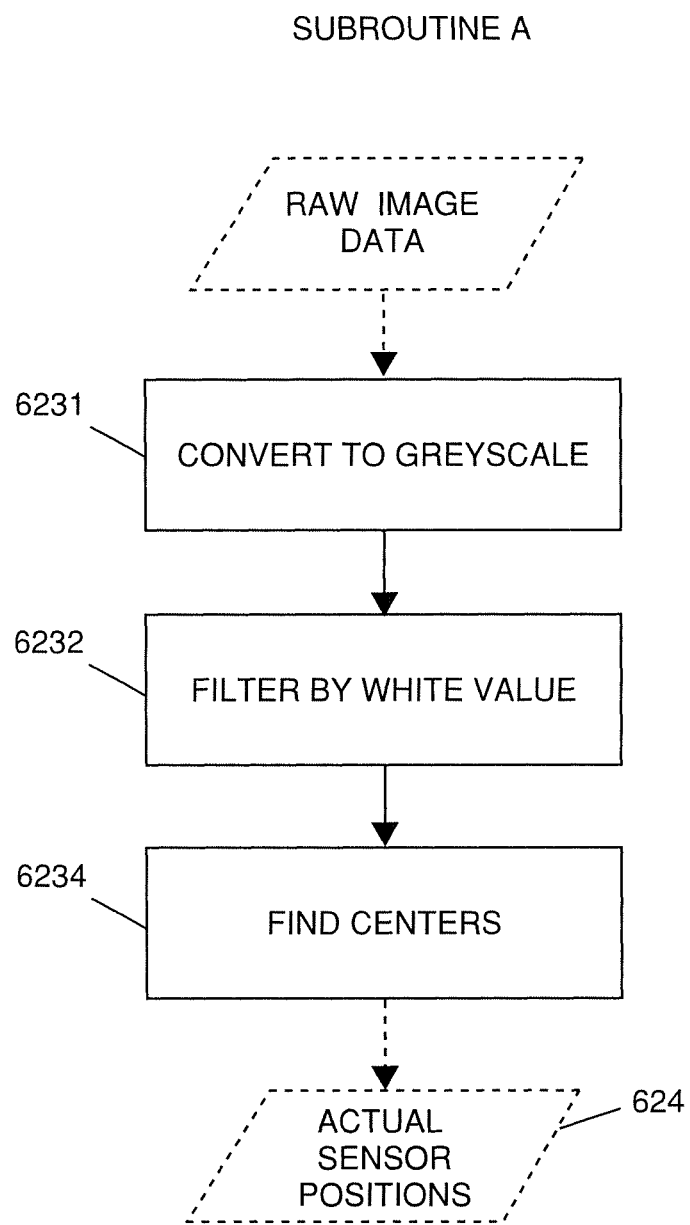
FIG. 6C is a flowchart of an exemplary subroutine for the image processing step of the procedure in FIG. 6B.

FIG. 6C illustrates an exemplary Subroutine A compatible with sensors that provide a unique light signature. The light signature for each LED can be of any wavelength(s) that are detectable by the image capture device. For instance, visible light is generally suitable. Alternatively, infrared energy or other portions of the electromagnetic spectrum outside the visible spectrum may be used for embodiments in which it is desirable for the light signature to be unobtrusive and unnoticed by the subject (since the wavelength is not detected by the human eye). The raw image data from the image capture device (block 601'), if a color image, is converted to greyscale (block 6231). Individual pixels or groups of pixels are then filtered by white value (block 6232). The filter threshold is preset such that that the light signatures for the sensors exceed the threshold and ambient light reflecting off of the subject and his/her clothing is below the threshold. This yields a processed image in which only circles of light remain, where the circles of light correspond with sensors. The center of each circle is found (block 6233). These centers are output as the actual sensor positions 624. As an alternative to the example Subroutine A, other object recognition procedures for digital image processing may be used. Existing image-processing libraries such as OpenCV and EmguCV are suitable for use in some implementations of sensor tracking 523.

Figure 6D:
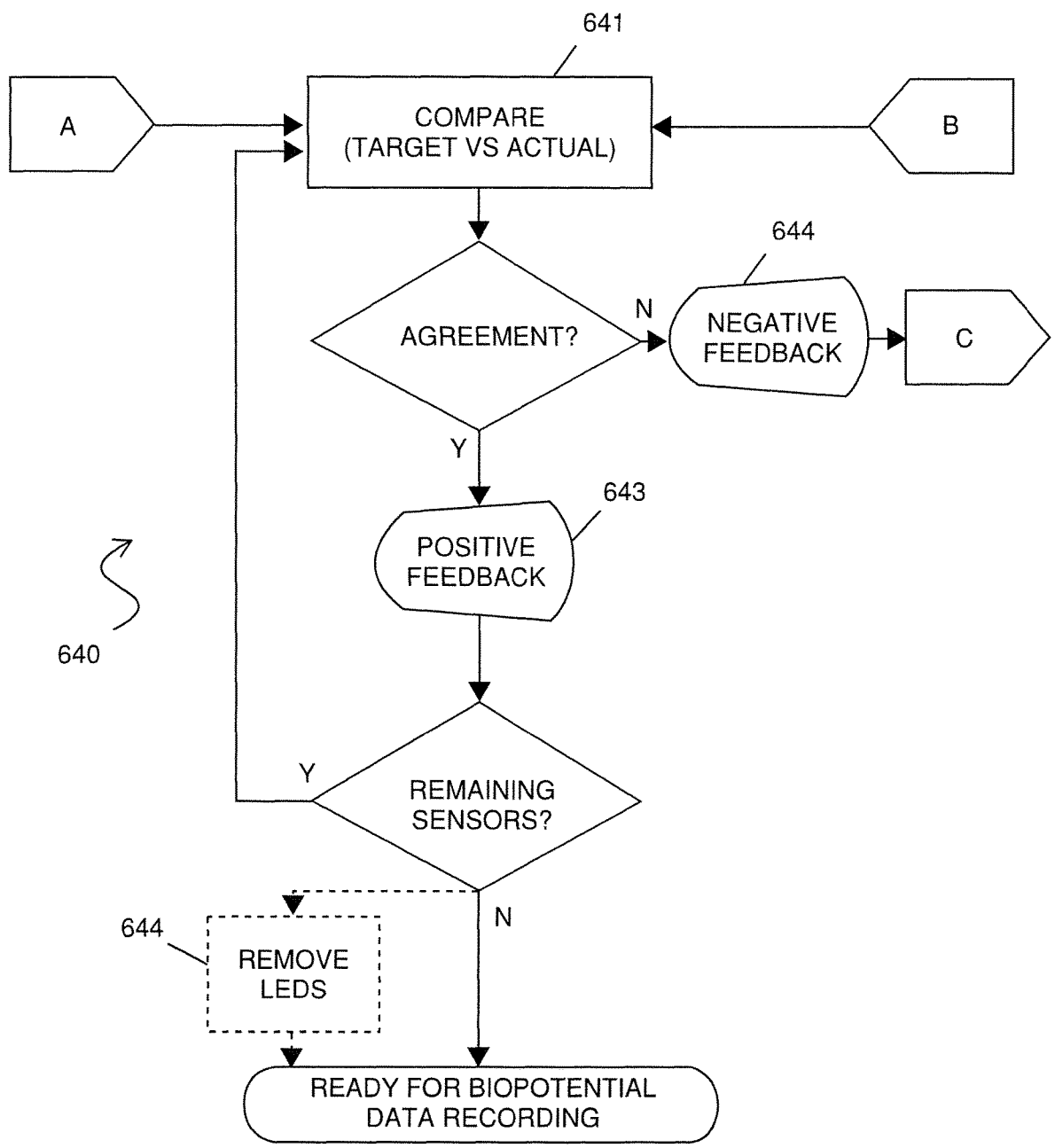
FIG. 6D is a flowchart of an exemplary procedure for sensor placement based on input from the anatomy tracking and sensor tracking procedures of FIGS. 6A and 6B, respectively.

FIG. 6D shows an exemplary process 640 for sensor placement 522 (FIG. 5). The process 640 is particularly influential with respect to the feedback provided to the subject/user. Using the target sensor positions 613 from the anatomy tracking procedure 600 and the actual sensor positions from the sensor tracking procedure 620, a comparison is made for equivalence within predetermined acceptable tolerances (block 641). For any one sensor, if the actual sensor position agrees (i.e., is identical within a predetermined tolerance or threshold) with the target sensor position, positive feedback is generated from the processing elements (e.g., processors) of the system. This positive feedback is transmitted (via wire and/or wirelessly) to an output device for display to the subject or user (block 643). Similarly, if the actual sensor position does not agree (i.e., the difference is outside a predetermined tolerance or threshold) with the target sensor position, negative feedback is generated from the processing elements (e.g., processors) of the system, and the negative feedback is transmitted (via wire and/or wirelessly) to the output device for display to the subject or user (block 644). In general, the comparison 641 is performed for every sensor and target sensor position present within the captured image of the subject. It is preferable that the comparison 641 be performed for every sensor necessary for a given bio-signal recording. However, some sensor positions have greater criticality than other sensor positions. Accordingly, it is not strictly necessary in all implementations that all sensors be subjected to the placement procedure 640. For a 12 lead ECG setup, it is preferable that at least the placement of sensors for positions V1 through V6 is achieved with the procedure 640. According to an exemplary embodiment, sensor position is capable of being located with an accuracy of <±2 cm on the human thorax. Some other exemplary tolerances for agreement in the case of positions V1 through V6 for a 12 lead ECG setup are ±2.0 cm, more preferably ±1.5 cm, most preferably ±1.0 cm or less. Acceptable tolerances or thresholds may be preset and differ for alternative implementations of the invention.

Figure 8:
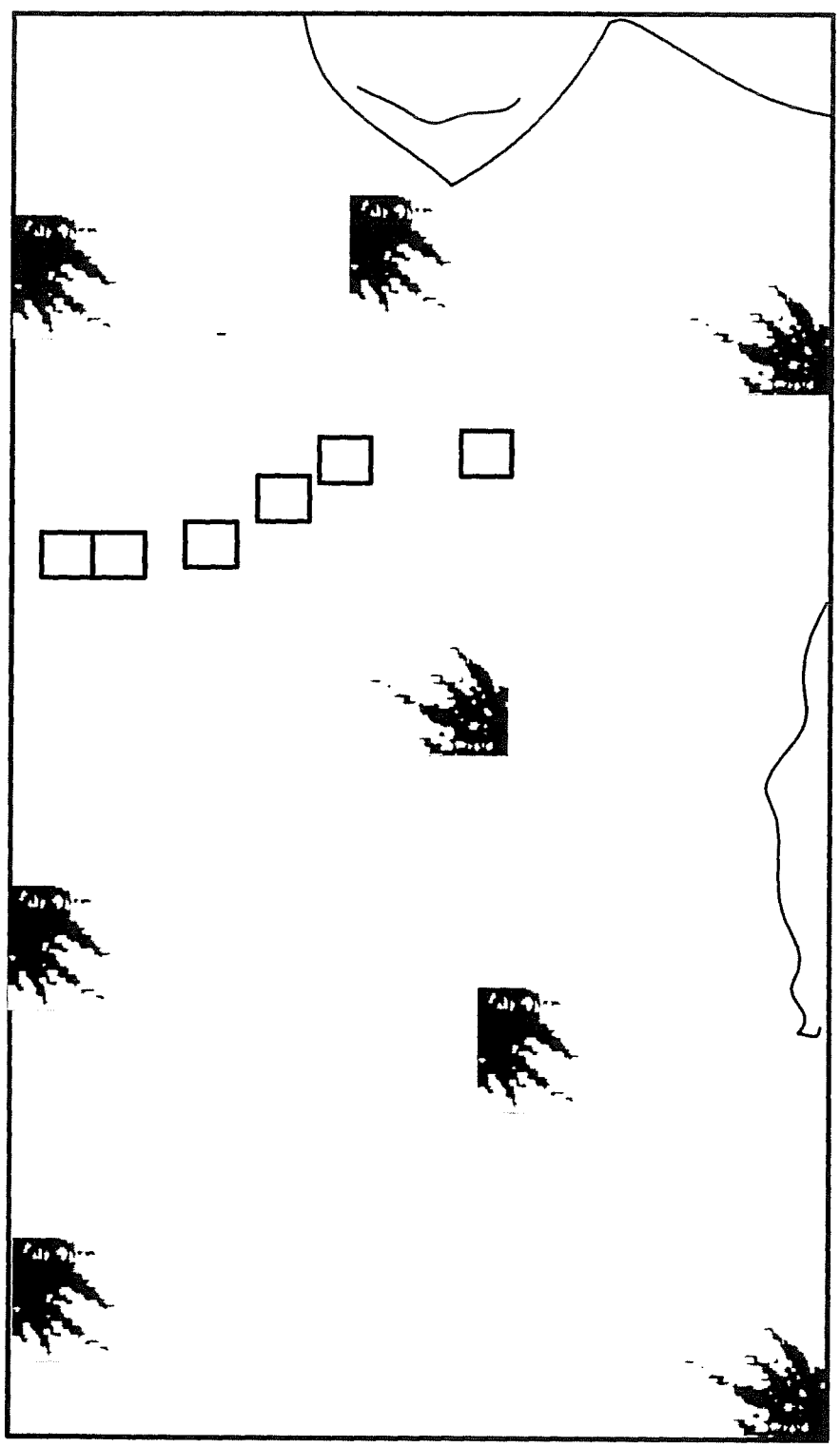
FIG. 8 shows an example graphic output using color changing indicia to indicate target sensor locations for an ECG and agreement with actual sensor locations.

FIG. 8 illustrates a representative sample of feedback displayed at either block 643 or 644 of FIG. 6D. In this example, a display of an output device shows a reproduction of the captured image of the subject. In addition, feedback in the form of square indicia are superimposed on the image of the subject. The indicia are indicative of the target sensor positions, and the color of the indicia is indicative of whether agreement exists between an actual sensor position and the corresponding target sensor position. At the outset, all six indicia (one each for positions V1 through V6) are color-coded red. The red color is negative feedback generated and displayed at block 644 in FIG. 6D. When the user accurately positions a sensor "inside" any of the square indicia such that the actual sensor position and target sensor position agree, the feedback changes. In this example, a red square indicium (negative feedback) changes to a green square indicium (positive feedback). The positive feedback is generated and displayed at block 643 in FIG. 6D.

A variety of different forms of feedback may be used for positive and negative feedback at blocks 643 and 644 in FIG. 6D. The use of six color-changing square indicia superimposed on a real time image of the subject as in FIG. 8 is simply one example. In general, it is desirable that the feedback, both positive and negative, be as user friendly as possible. Different types of indicia (e.g., different shapes like square, circles, spots, triangles, cross-hairs; different color; or other indicia) may be used. Simply one, some, or all the indicia for all of the target sensor locations may be indicated at any given moment in time. As supplement to visual feedback, or as a substitute for visual feedback (especially in the case of visually impaired individuals), the positive and negative feedback may include audio instructions guiding the placement of each sensor. For example, the system can instruct the user to move a sensor X distance up, down, right, or left on his or her body to bring the actual sensor position into agreement with the target sensor position, where X is the total discrepancy (e.g., in centimeters or inches) between the two positions under comparison.

Figure 9A:
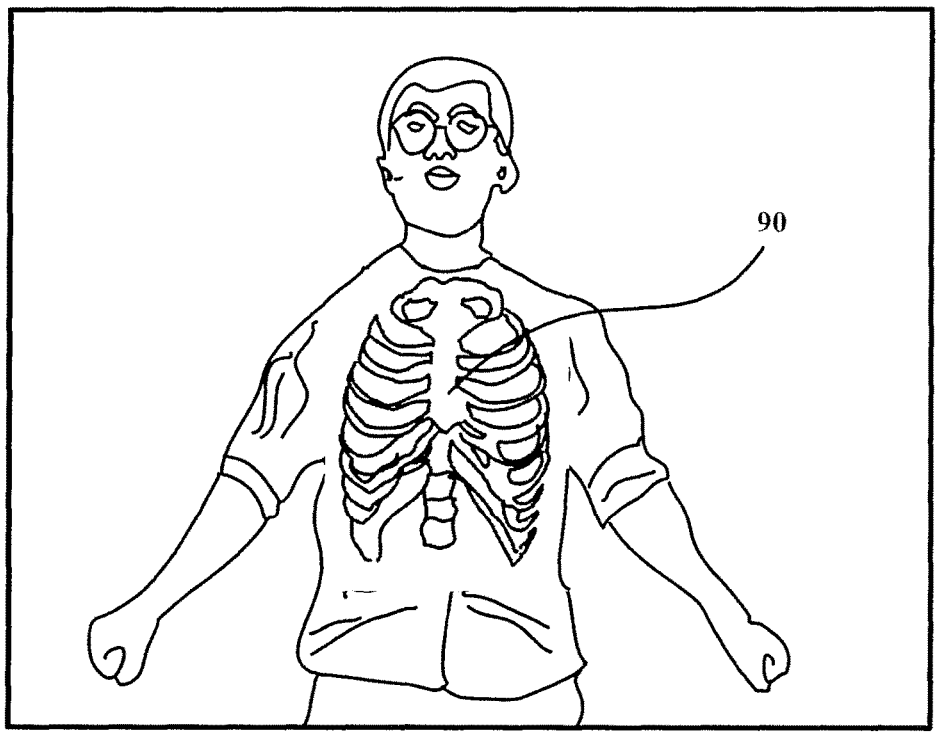
FIG. 9A shows example visual feedback on a graphical user interface (GUI). The feedback is based on algorithmically derived anatomical localization.
Figure 9B:
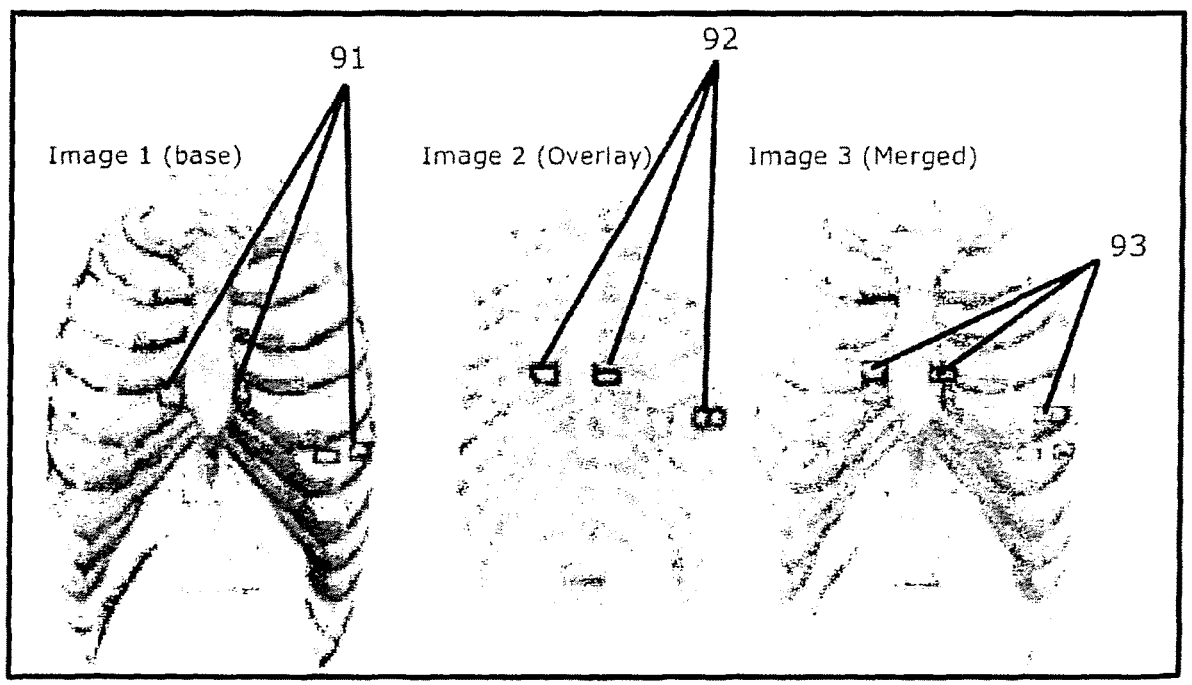
FIG. 9B shows example visual feedback on a GUI. Sensors are shown overlaid with an image and merged to provide the localization. Such captured merged images results in minimal errors in terms of exact position with the algorithms herein increasing the accuracy of the merged images.

FIGS. 9A and 9B provide further examples of feedback provided to a subject or user in some embodiments. FIG. 9A shows how a novel image processing algorithm according to the teachings herein registers and aligns a reference image 90—in this case a depiction of the rib cage—with a real-time image of the subject from an image capture device, such as, for example, a Kinect® sensor to provide anatomical localization. To further localize and detect the anatomical structures, localization algorithms suitable for a resource-constrained system are utilized with low bandwidths. The reference image 91 included with the feedback to the subject may be, for example, a skeletal structure, another anatomical structure other than a skeletal structure, or some other image altogether. FIG. 9B shows additional details of a working methodology in which target sensor positions 91 are overlaid with an image 92 and merged 93 to provide the localization. Such captured merged images results in minimal errors in terms of exact position with the algorithms herein increasing the accuracy of the merged images. The identification of the target sensor positions (e.g., for the placement of non-contact electrodes) on the human body is achieved without human intervention.

Returning to FIG. 6D, connector C bridging FIG. 6D back to FIG. 6B illustrates the feedback loop by which the system continuously monitors the subject's progress in placing each sensor. The actual sensor position is continuously monitored in real time, with the result that the subject receives an immediate (or substantially immediate) change from negative feedback to positive feedback when he/she successfully positions the sensor so that it is in agreement with the target sensor position. Accurately placed sensors also continue to be monitored with the effect that, in the event a user displaces a successfully positioned sensor, negative feedback is again generated to indicate to the subject that the sensor requires repositioning once more.

The processes of FIGS. 6A through 6D are performed in real time (or substantially real time, at least to the perception of a human user) for all the sensors necessary for a given bio-signal recording. If some sensors are positioned at substantial distances from one another, groups of sensors common to the same portion of the subject's body (e.g., just the head, just the chest or thorax, just a single limb, just the legs, etc.) may be addressed concurrently while other sensors on a different part of the body are addressed subsequently. For instance, in the case of a 12 lead ECG setup, the processes of FIGS. 6A through 6D can be performed substantially at the same time for all six sensors for positions V1 through V6. The remaining fours sensors which are not positioned on the subject's thorax can also be addressed at the same time if, for example, the image capture device is imaging the user's entire body. Alternatively, the remaining four sensors may be addressed after or before the sensors for V1 through V6. The precise ordering, sequence, or concurrency with which feedback is provided to the user for two or more sensors may be highly variable depending on the desired implementation. For some users, such as children, instructing the positioning of just one sensor at a time may be chosen to reduce confusion and distraction.

The comparison loop of FIG. 6D is complete when the there are no remaining sensors that disagree with a respective target sensor location. At this point, sensor placement is complete and data recording for the bio-signal (e.g., biopotential) begins. Optional block 644, indicated in broken lines, indicates that in the circumstance that removable LEDs or other sensor tracking signal device were attached to the sensors (e.g., at block 621 of FIG. 6B), they can be removed if desired.

Returning to FIG. 4, bio-signal recording and processing is performed using the sensors 401, signal processing circuitry 406 (frequently but not necessarily analog) built-in with an electrode of each sensor, and circuitry and/or digital processors 408 which communicate with the sensor circuitry preferably by wireless communication using transmitters, receivers, transceivers 407, and/or one or more networks.

Figure 10B:
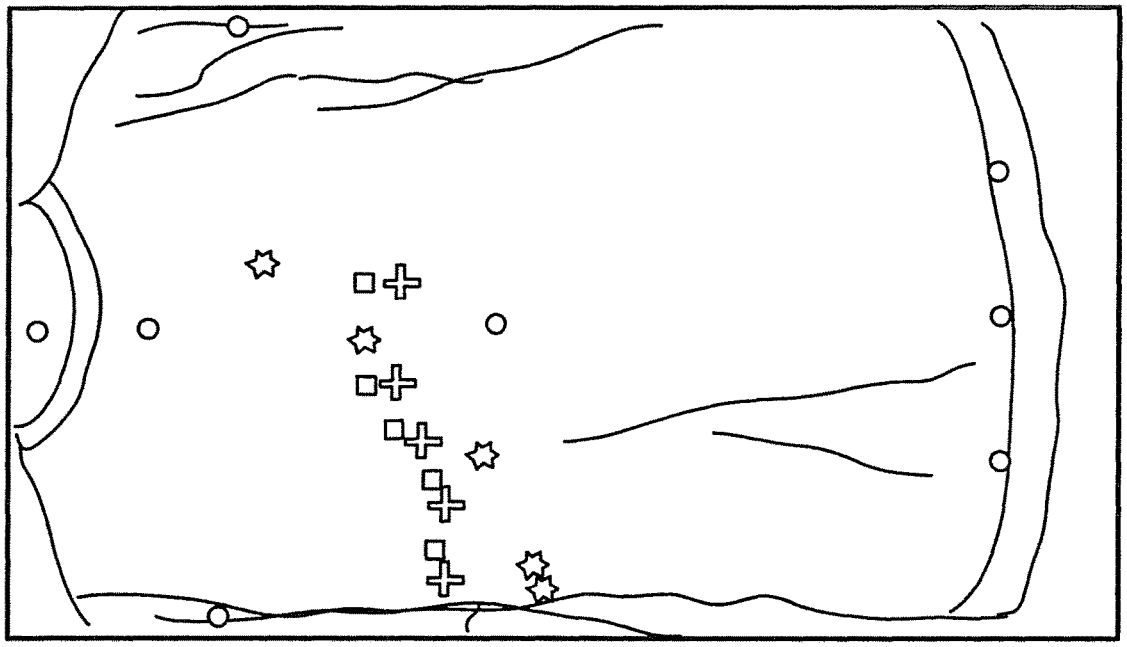
FIGS. 10A and 10B show the inconsistencies among different human users when estimating target sensor locations as compared to an exemplary automated system according to an embodiment of the invention.
Figure 10A:
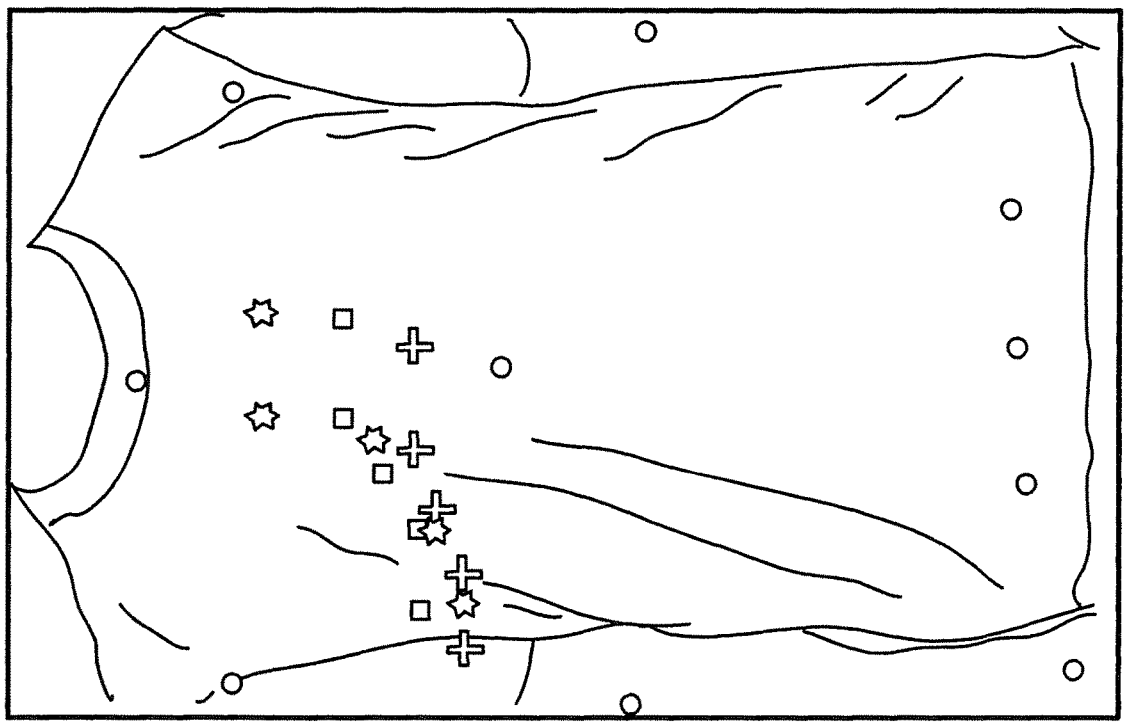

FIGS. 10A and 10B provide illustrative context as to the improved precision of sensor placement in accordance with exemplary methods and system herein. Both figures show images of separate subjects standing before an image capturing device such as a Microsoft® Kinect®. In both figures, an image (e.g., video) was captured of the subject's thorax with the objective of placing non-contact electrodes for positions V1-V5 of a 12 lead ECG. The circle indicia superimposed on the images are anatomical reference points determined in accordance with procedure 600 of FIG. 6A. The cross-hair indicia are target sensor positions likewise determined in accordance with procedure 600 of FIG. 6A. The star indicia show the sensor positions estimated by a first doctor, and the square indicia show the sensor positions estimated by a second doctor. The two subjects have similar anatomical characteristics such as height, stature, posture, and shoulder widths. Provided this physical similarity, the target sensor positions selected according to the exemplary system and methods disclosed herein are quite similar, as apparent by comparison of the cross-hair indicia in FIG. 10A with the cross-hair indicia in FIG. 10B. In stark contrast, the sensor positions determined by different doctors differed substantially between the two doctors for any one subject and between the two subjects for any one doctor. For instance, it is apparent from FIG. 10A alone that many of the sensor positions selected by the first doctor (star indicia) are in substantial disagreement with the sensor positions selected by the second doctor (square indicia). Neither of the two doctors' estimations correspond with the computer-assisted placement target sensor positions (cross-hair indicia). Comparing FIGS. 10A and 10B, it is apparent that despite the similarities in the anatomy and biometrics of the two subjects, the first doctor (star indicia) estimated considerably different positions from one patient to the other. The second doctor (square indicia), though showing more consistency than the first doctor, also clearly deviated in his placement from one patient to the other. The computer-assisted positions (cross-hair indicia) show appreciable consistency from one subject to the other subject.

Figure 11:
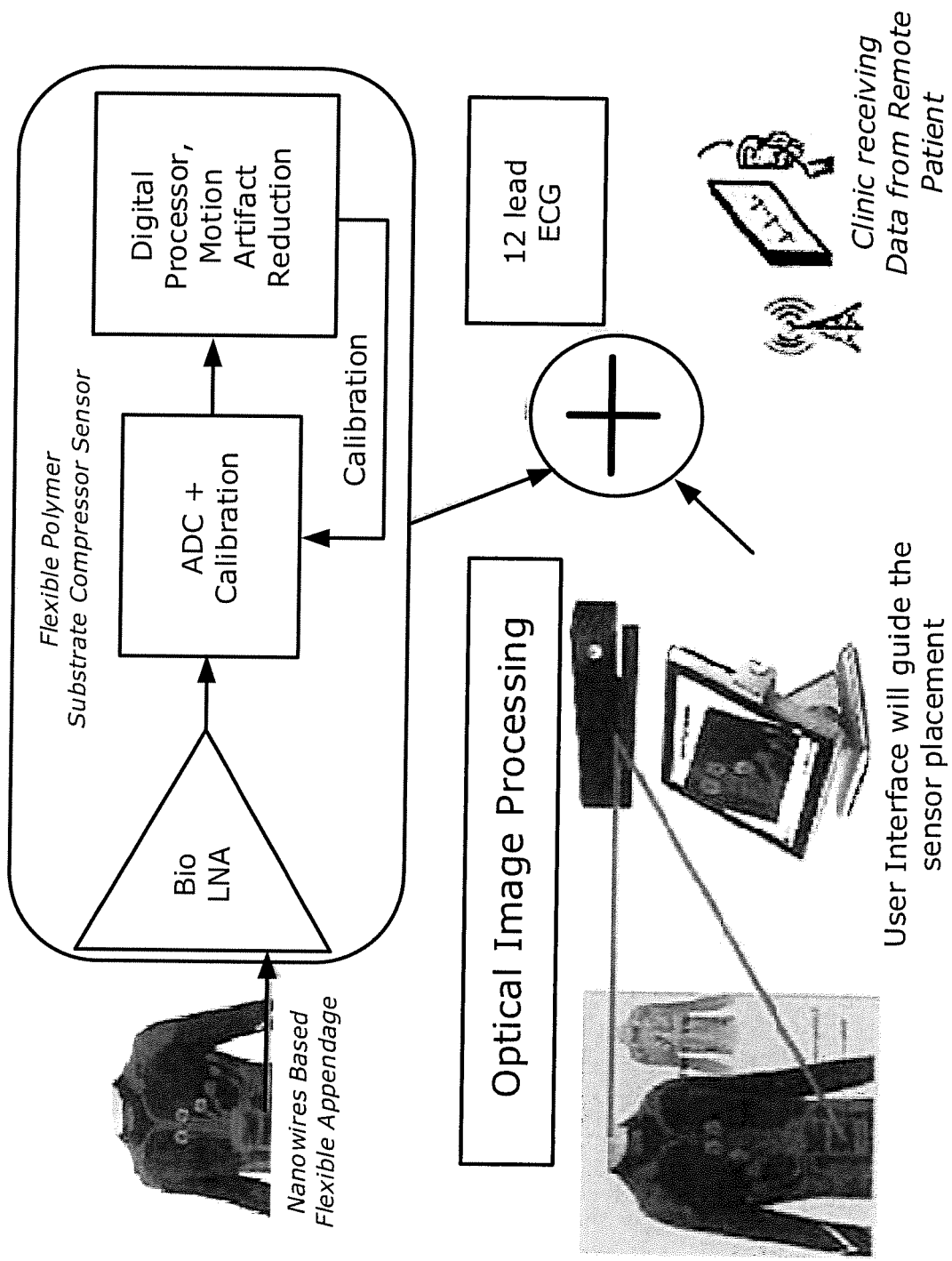
FIG. 11 shows an example system architecture for setup and recording of an ECG.

FIG. 11 shows an example architecture of a 12-lead ECG system. The architecture includes ADC calibration for higher dynamic range and motion artifact correction on-chip. The digital processor for generating ECG response and the wireless radio is shown integrated on the flex-PCB board (outside the chip) and the focus is realized on a low-power 12-channel system with a dynamic range >10 bits and power consumption <1 mW (not including off-chip components). To realize this with minimal power consumption, compressive sensing schemes along with polyphase adaptive calibration schemes may be used. To make the design conformal to human body shapes, the design is configured (e.g., imprinted) on a flexible organic polymer substrate. A software interface displays the wireless ECG obtained and verifies the link to a remote doctor.

It is to be appreciated that motion artifact correction performed on a recorded bio-signal can also include data from accelerometers worn by the subject. This provides accurate measurement of motion applied to the wearable material and devices disclosed herein.

It is to be appreciated that analog signal processing is combined with spatial accuracy achieved using image processing algorithms to achieve higher accuracy for medical use ECG signal.

According to an aspect of some exemplary embodiments, the sensors (e.g., sensors 401 in FIG. 4) are non-contact electrodes. The positioning of the sensors afforded by systems and methods according to the teachings herein provide the level of accuracy and precision necessary for reliable signals from non-contact electrodes. As was discussed above, non-contact electrodes are much more susceptible to errors and inconsistencies arising from improper or inconsistent sensor placement as compared to wet contact electrodes, for example. While systems and methods according to embodiments of the invention are especially well suited for non-contact electrodes, most if not all bio potential recording procedures (ECG, EEG, EMG, etc.) would benefit from the assisted sensor placement described, regardless of the type of sensor used (e.g., wet, dry, insulated, non-contact, etc.).

Figure 12:
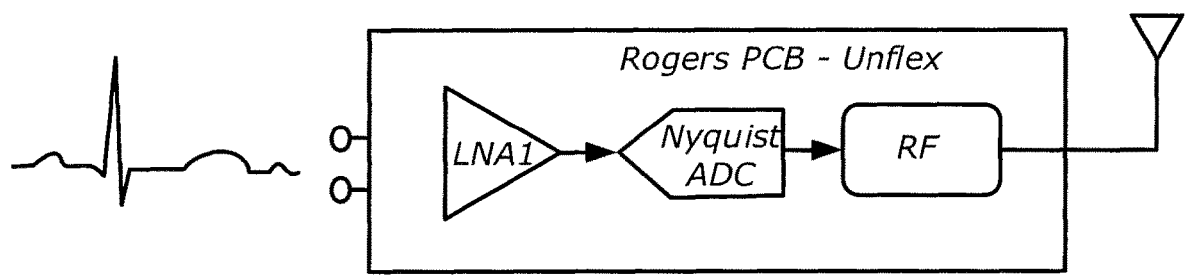
FIG. 12 shows a silicon sensor design configured with a low-noise amplifier (LNA), analog-to-digital converter (ADC) and a digital processor (DP).

Sensors for body-area networks have evolved from a simple transducer and an amplifier to a miniaturized low-power radio that can sense the required external parameter (for e.g., temperature, ECG signal, etc.), amplify the signal with sufficient isolation, digitize the signal, provide any further processing, and then transmit it wirelessly for recordation and/or further use (e.g., medical diagnosis). FIG. 12 shows a typical silicon sensor design with a few important features shown in blocks. These features include a low-noise amplifier (LNA), analog-to-digital converter (ADC), and a digital processor (DP). All of these features may be provided on-chip for a wearable non-contact sensor positioned and worn by the user.

Key signal features may be acquired using a Nyquist-rate analog-to-digital conversion without exploiting the typical bio-signal characteristic of sparsity in some domain (e.g., time, frequency, etc.). Alternative, compressive sensing (CS) may be used, whereby this sparsity is exploited for commensurate power savings by enabling alias-free sub-Nyquist acquisition. A sample design, illustrated in FIG. 13, uses a 2 mm×3 mm area and consumes only 2 µW (worst-case) which is 2-3× lower than conventional designs.

Figure 13:
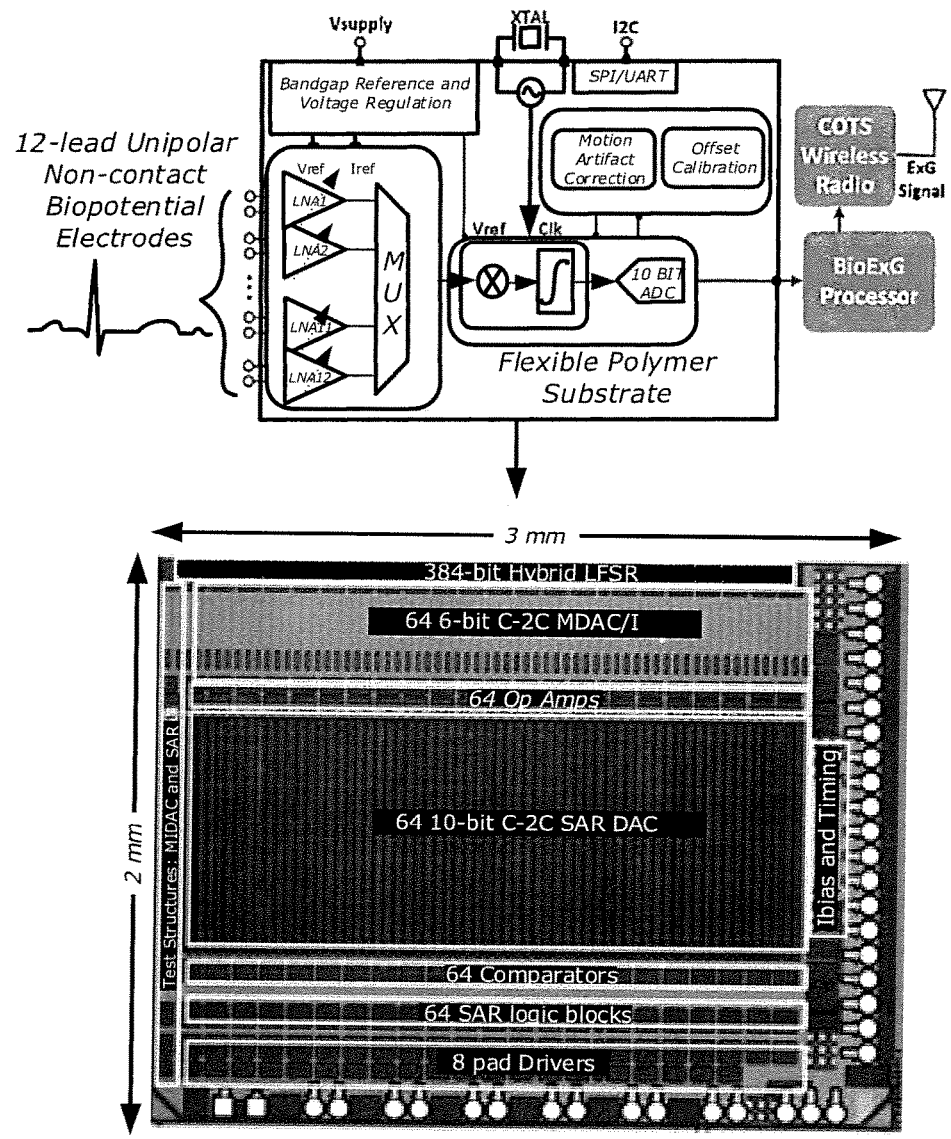
FIG. 13 shows a general schematic and design of a novel low power sensor design with Transmitter/Receiver (Tx/Rx) wireless link and encryption capability.

FIG. 13 shows a general schematic and resultant design of a novel low power sensor design with a transmitter/receiver (Tx/Rx) wireless link and encryption capability. The configuration improves analog front-end by calibrating the ADC for motion artifacts and analog dc offsets which can significantly affect the dynamic range of the sensor. Embodiments may also include a custom bio-Low Noise Amplifier (bio-LNA) on a flexible substrate that can interface with such an analog-to-digital converter. An array of these sensors is capable of being used for the 12-lead ECG disclosed herein.

Flexible sensor array are desirable and allow for extended bio-signal recording while a subject goes about other daily activities. Long term recording may be facilitated by ultra-low power on CMOS sensors.

Custom non-contact bio-sensors may be used in some embodiments. Alternatively, known non-contact sensors may be used, such as disclosed by U.S. Pat. No. 8,694,084, incorporated herein by reference.

Example data processing algorithms performed on the data collected by the bio-signal sensors may but do not necessarily include: averaging of a plurality of signals over a period of time (up to 20 seconds or longer) to collect sufficient cardiac beats, mathematical analysis, mappings and projections, transforms to include Fourier transforms, Laplace transforms, and Hilbert transforms, mathematical correlations, and statistical methods.

The wearable article 402 (e.g., of clothing) from FIG. 4 to which the sensors are attached for recording bio-signals is preferably made to conform to the surfaces of the subject, at least at/near each target sensor location. Flexible and contractile fabrics are good examples. The modality by which the sensors are attachable and repositionable to the article may vary among embodiments. For example, one suitable means for attachment that permits variable positioning is a hook-and-loop configuration (e.g., Velcro®). Hooks may be provided on an underside of a sensor and the article may include loops either added to or inherent in a fabric or material of the article.

Because a human subject is capable of constantly being linked to a virtual world in today's world, an advantageous aspect of some embodiments is utilization of reusable, flexible and even machine-washable electronic textile wear suitable for both adolescents and adults. Such electronic textile wear includes configured fabricated printed circuits on textile using nanowires that are intrinsically flexible and suitable for textiles.

Figure 14A:
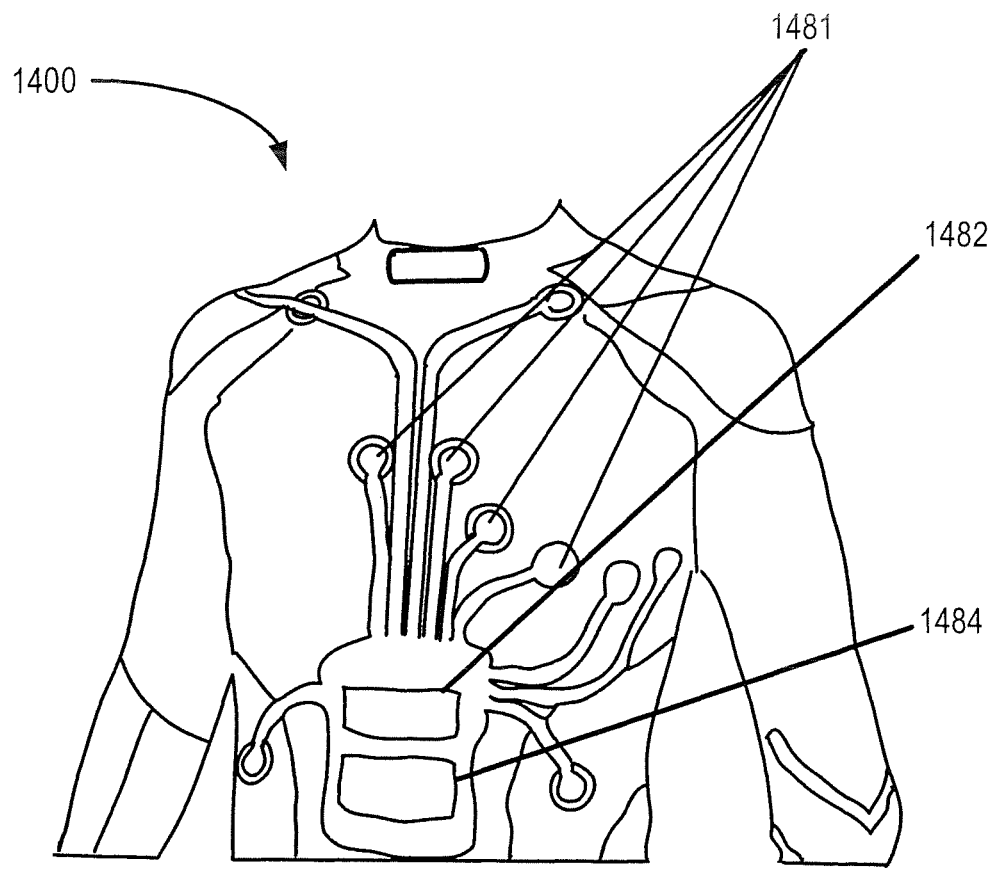
FIG. 14A shows an example conformal e-textile with reconfigurable locations for sensors, battery, and antenna(s).

FIG. 14A shows details of an example conformal e-textile 1400 with reconfigurable locations for sensors 1481, a battery 1482, and antenna(s) 1484. Such a conformal arrangement creates generic use for different body shapes and form features.

Figure 14B:
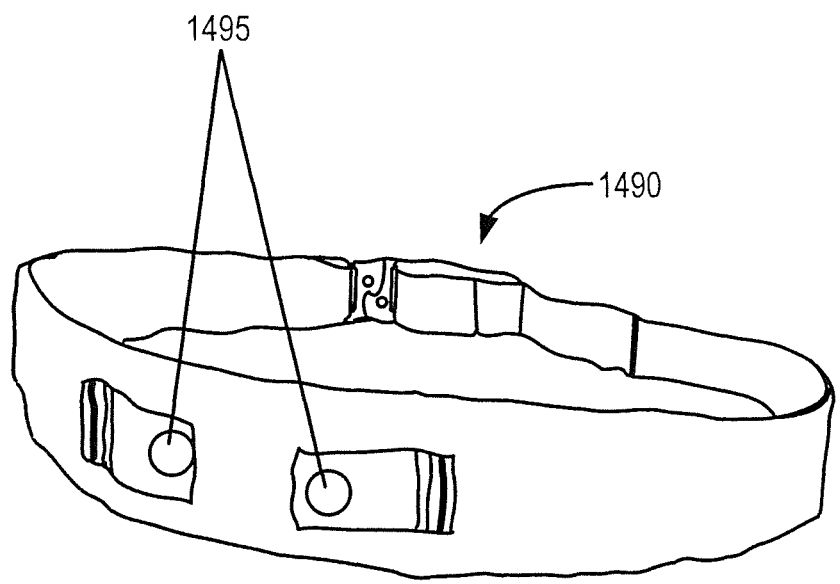
FIG. 14B shows a belt for attaching non-contact sensors.

An alternative embodiment includes an article that is a belt for an ECG measurement or a head-cap (not shown) for an EEG. FIG. 14B shows an example depiction of the strap-on belt-like article 1490 showing a 2-sensor 1495 configuration. While FIG. 14B shows only a 2-sensor configuration, it is also to be appreciated that other numbers of sensors (e.g., up to at least 6 sensors) can also be configured with the embodiments herein, including a strap-on or belt configuration.

Components disclosed herein within a configured system or other embodiments disclosed herein may be implemented by a controller and data system of various circuitry. Such a controller and data system may be in the form of a desktop computer, laptop computer, a network server, a server computer, or may be implemented by any one of or a combination of general or special-purpose processors (digital signal processor (DSP)), firmware, software, and/or hardware circuitry to provide instrument control, data analysis, etc., for the example configurations disclosed herein.

Individual software modules, components, and routines may also often be utilized by disclosed systems in the form of a computer program, procedure, or process written in a suitable programming language, e.g. Java, C, C #, C++. In addition, the computer programs, procedures, or processes may be compiled into intermediate, object, or machine code and presented for execution as instructions and control functions so as to be implemented by a disclosed system herein, or any other configurations disclosed herein. Various implementations of the source, intermediate, and/or object code and associated data may also be stored in one or more computer readable storage media that include read-only memory, random-access memory, magnetic disk storage media, optical storage media, flash memory devices, and/or other suitable media. As used herein, the term "computer readable storage media" excludes propagated signals, per se and refers to media known and understood by those of ordinary skill in the art, which have encoded information provided in a form that can be read (i.e., scanned/sensed) by a machine/computer and interpreted by the machine's/computer's hardware and/or software.

It is to be understood that the invention is not limited to the various example embodiments disclosed herein. Other embodiments that use alternative combinations of features of embodiments disclosed herein are possible without departing from the spirit and scope of the invention. Although different selected embodiments have been illustrated and described in detail, it is to be appreciated that they are exemplary, and that certain substitutions and alterations are possible without departing from the spirit and scope of the present invention.

We claim:

1. A system for assisted sensor placement for bio-signal monitoring, comprising:
   a plurality of sensors fixable to an article worn by a subject, wherein said sensors are configured to detect one or more bio-signals and wherein said sensors are non-contact electrodes;
   an imaging device positioned at a distance from the subject configured to capture an image of the subject;
   one or more computer-readable storage media containing anatomical reference data and computer-readable instructions; and
   one or more processors that, upon execution of the computer-readable instructions, perform steps comprising
      determining target sensor positions on the article worn by the subject based on subject anatomy in the image captured with the imaging device and the anatomical reference data,
      determining actual sensor positions of the plurality of sensors, and comparing the target sensor positions with the actual sensor positions; and an output device for providing results of the comparison to the subject, wherein the imaging device is configured to capture an image of at least a thoracic region of the subject, and wherein the plurality of non-contact sensors includes at least six electrodes for positions V1 to V6 of a twelve lead electrocardiogram (ECG).

2. The system of claim 1, wherein the output device is a display for showing the results of the comparison to the subject on a screen.

3. The system of claim 1, wherein the one or more processors perform the step of determining actual sensor positions based on image processing of the image captured with the imaging device.

4. The system of claim 3, wherein the plurality of sensors include light emitting diodes (LEDs), and wherein the one or more processors determine the actual sensor positions by converting the image captured with the imaging device to greyscale, filtering the greyscale image based on white value, finding centers of remaining circles which correspond to light from the LEDs, and equating the actual sensor positions to the centers.

5. The system of claim 1, wherein the plurality of sensors are electrodes configured to record data for one or more of an electrocardiogram (ECG), electroencephalogram (EEG), electromyogram (EMG), electrooculogram (EOG), and galvanic skin response (GSR).

6. The system of claim 1, wherein the one or more processors further perform, upon execution of the computer-readable instructions, generating feedback indicative of agreement between target sensor positions and actual sensor positions, wherein said feedback is included in the results provided by the output device.

7. The system of claim 1, wherein the output device is configured to include in its output one or more of the captured image of the subject, indicia for target sensor positions, and a color or a shape that changes upon agreement between a target sensor position and actual sensor position.

8. The system of claim 1, wherein the imaging device comprises a plurality of cameras and one or more processors configured to detect depth based on a combination of two-dimensional images captured from different orientations with respect to the subject.

9. A method of assisted sensor placement for bio-signal monitoring, comprising:

capturing an image of a subject with an imaging device positioned at a distance from the subject, determining target sensor positions for a plurality of sensors on an article worn by the subject based on subject anatomy in the image captured with the imaging device and anatomical reference data, determining actual sensor positions of the plurality of sensors;

comparing the target sensor positions with the actual sensor positions; and displaying feedback to the subject indicative of agreement between the target sensor positions and actual sensor positions, wherein said sensors are configured to detect one or more bio-signals and wherein said sensors are non-contact electrodes, wherein the capturing step captures an image of at least a thoracic region of the subject, and wherein the determining steps determine target and actual sensor positions for at least six non-contact electrodes for positions V1 to V6 of a twelve lead electrocardiogram (ECG).

10. The method of claim 9, wherein the displayed feedback includes one or more of the captured image of the subject, indicia for target sensor positions, and a color or a shape that changes upon agreement between a target sensor position and actual sensor position.

11. The method of claim 9, wherein the determining steps determine target and actual sensor positions for a plurality of non-contact electrodes configured to record data for one or more of an electrocardiogram (ECG), electroencephalogram (EEG), electromyogram (EMG), electrooculogram (EOG), and galvanic skin response (GSR).

12. The method of claim 9, wherein the step of determining actual sensor positions is based on image processing of the image of the subject captured with the imaging device.

13. A computer-implemented method for assisted sensor placement for bio-signal monitoring, involving one or more processors that, upon execution of computer readable instructions, perform the method steps of:

determining target sensor positions for a plurality of non-contact sensors on an article worn by the subject based on subject anatomy in an image of the subject and anatomical reference data;

determining actual sensor positions of the plurality of non-contact sensors;

comparing the target sensor positions with the actual sensor positions; and generating feedback for the subject indicative of agreement between target sensor positions and actual sensor positions, wherein said sensors are configured to detect one or more bio-signals and wherein said sensors are non-contact electrodes, wherein the determining steps determine target and actual sensor positions for at least six non-contact electrodes for positions V1 to V6 of a twelve lead electrocardiogram (ECG).

14. The method of claim 13, wherein the generated feedback includes data corresponding to one or more of the captured image of the subject, indicia for target sensor positions, and a color or a shape that changes upon agreement between a target sensor position and actual sensor position.

15. The method of claim 13, wherein the determining steps determine target and actual sensor positions for a plurality of non-contact electrodes configured to record data for one or more of an electrocardiogram (ECG), electroencephalogram (EEG), electromyogram (EMG), electrooculogram (EOG), and galvanic skin response (GSR).

16. The method of claim 13, wherein the step of determining actual sensor positions is based on image processing of the image of the subject.

* * * * *